United States Patent
Saxonov et al.

(10) Patent No.: US 8,663,920 B2
(45) Date of Patent: Mar. 4, 2014

(54) LIBRARY CHARACTERIZATION BY DIGITAL ASSAY

(75) Inventors: Serge Saxonov, Oakland, CA (US);
Svilen S. Tzonev, Pleasanton, CA (US);
Michael Y. Lucero, South San Francisco, CA (US); Ryan T. Koehler, West Linn, OR (US); Benjamin J. Hindson, Livermore, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/562,198

(22) Filed: Jul. 30, 2012

(65) Prior Publication Data

US 2013/0045875 A1    Feb. 21, 2013

Related U.S. Application Data

(60) Provisional application No. 61/513,474, filed on Jul. 29, 2011, provisional application No. 61/601,514, filed on Feb. 21, 2012.

(51) Int. Cl.
*C12Q 1/68* (2006.01)
*C40B 30/00* (2006.01)
*C40B 30/04* (2006.01)

(52) U.S. Cl.
USPC .............. 435/6.1; 435/6.11; 435/6.12; 506/7; 506/9

(58) Field of Classification Search
USPC ................................................. 506/7; 435/6.1
See application file for complete search history.

(56) References Cited

U.S. PATENT DOCUMENTS

| | | |
|---|---|---|
| 3,575,220 A | 4/1971 | Davis et al. |
| 4,051,025 A | 9/1977 | Ito |
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |

(Continued)

FOREIGN PATENT DOCUMENTS

| | | |
|---|---|---|
| EP | 1 522 582 A2 | 4/2005 |
| EP | 1 522 582 B1 | 4/2007 |

(Continued)

OTHER PUBLICATIONS

Shendure et al., "Next-generation DNA sequencing," Nature Biotechnology 2008, 26:1135-1145.*

(Continued)

*Primary Examiner* — Samuel Woolwine
*Assistant Examiner* — Kaijiang Zhang
(74) *Attorney, Agent, or Firm* — Kolisch Hartwell, P.C.

(57) ABSTRACT

Methods of characterizing a nucleic acid library by digital assay.

33 Claims, 8 Drawing Sheets

(56) References Cited

U.S. PATENT DOCUMENTS

| | | |
|---|---|---|
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |

(56) References Cited

U.S. PATENT DOCUMENTS

| | | |
|---|---|---|
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| GB | 1 503 163 | 3/1978 |
| GB | 2 097 692 | 11/1982 |
| JP | 0295433 | 4/1990 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12327 | 2/2001 |
| WO | 02/23163 | 3/2002 |
| WO | 02/060584 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03/072258 | 9/2003 |
| WO | 2004/040001 | 5/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |

(56) References Cited

FOREIGN PATENT DOCUMENTS

| | | |
|---|---|---|
| WO | 2006/038035 | 4/2006 |
| WO | 2006/086777 | 8/2006 |
| WO | 2006/095981 | 9/2006 |
| WO | 2007/091228 | 8/2007 |
| WO | 2007/091230 | 8/2007 |
| WO | 2007/092473 | 8/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008/070074 | 6/2008 |
| WO | 2008/070862 | 6/2008 |
| WO | 2008/109176 | 9/2008 |
| WO | 2008/109878 | 9/2008 |
| WO | 2008/112177 | 9/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2010/001419 | 1/2010 |
| WO | 2010/018465 | 2/2010 |
| WO | 2011/034621 | 3/2011 |
| WO | 2011/079176 | 6/2011 |

OTHER PUBLICATIONS

Huang et al. "Rapid Screening of Complex DNA Samples by Single-Molecule Amplification and Sequencing." 2011 PLoS ONE 6(5); e19723. doi:10.1371/journal.pone.0019723.

Young, Lee W., Authorized officer, International Searching Authority, International Search Report, PCT Patent Application Serial No. PCT/US2012/048892; search date: Sep. 29, 2012; mail date: Oct. 22, 2012.

Young, Lee W., Authorized officer, International Searching Authority, Written Opinion of the International Searching Authority, PCT Patent Application Serial No. PCT/US2012/048892; opinion date: Sep. 29, 2012; mail date: Oct. 22, 2012.

J. Smid-Korbar et al., "Efficiency and usability of silicone surfactants in emulsions," International Journal of Cosmetic Science 12, pp. 135-139, (1990), presented at the 15$^{th}$ IFSCC International Congress, Sep. 26-29, 1988, London.

A. Chittofrati et al., "Perfluoropolyether microemulsions," Progress in Colloid & Polymer Science 79, pp. 218-225, (1989).

Steven A. Snow, "Synthesis and Characterization of Zwitterionic Silicone Sulfobetaine Surfactants," Langmuir, vol. 6, No. 2, American Chemical Society, pp. 385-391, (1990).

Polydimethylsiloxane, 5 pgs., published in FNP 52 (1992).

Russell Higuchi et al., "Kinetic PCR Analysis: Real-time Monitoring of DNA Amplification Reactions," Bio/Technology vol. II, pp. 1026-1030, Sep. 11, 1993.

D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).

Y. Sela et al., "Newly designed polysiloxane-graft-poly (oxyethylene) copolymeric surfactants: preparation, surface activity and emulsification properties," Colloid & Polymer Science 272, pp. 684-691, (1994).

M. Gasperlin et al., "The structure elucidation of semisolid w/o emulsion systems containing silicone surfactant," International Journal of Pharmaceutics 107, pp. 51-56, (1994).

Mieczyslaw A. Piatyszek et al., "Detection of telomerase activity in human cells and tumors by a telomeric repeat amplification protocol (TRAP)," Methods in Cell Science 17, pp. 1-15, (1995).

Anthony P. Shuber et al., "A Simplified Procedure for Developing Multiplex PCRs," Genome Research, published by Cold Spring Harbor Laboratory Press, pp. 488-493, (1995).

A. V. Yazdi et al., "Highly Carbon Dioxide Soluble Surfactants, Dispersants and Chelating Agents," Fluid Phase Equilibria, vol. 117, pp. 297-303, (1996).

Ariel A. Avilion et al., "Human Telomerase RNA and Telomerase Activity in Immortal Cell Lines and Tumor Tissues," Cancer Research 56, pp. 645-650, Feb. 1, 1996.

Shuming Nie et al., "Optical Detection of Single Molecules," Annu. Rev. Biophys. BiomoL Struct. vol. 26, pp. 567-596, (1997).

Edith J. Singley et al., "Phase behavior and emulsion formation of novel fluoroether amphiphiles in carbon dioxide," Fluid Phase Equilibria 128, pp. 199-219, (1997).

Olga Kalinina et al., "Nanoliter scale PCR with TaqMan Detection," Nucleic Acids Research, vol. 25, No. 10 pp. 1999-2004, (1997).

Zhen Guo et al , "Enhanced discrimination of single nucleotide polymorphisms by artificial mismatch hybridization," Nature Biotechnology vol. 15, pp. 331-335, Apr. 1997.

E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.

Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.

Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.

Bert Vogelstein et al., "Digital PCR," Proc. Natl. Acad. Sci. USA, vol. 96, pp. 9236-9241, Aug. 1999.

Anthony J. O'Lenick, Jr., "Silicone Emulsions and Surfactants," Journal of Surfactants and Detergents, vol. 3, No. 3, Jul. 2000.

N. Garti et al., "Water Solubilization in Nonionic Microemulsions Stabilized by Grafted Siliconic Emulsifiers," Journal of Colloid and Interface Science vol. 233, pp. 286-294, (2001).

Shinji Katsura et al., "Indirect micromanipulation of single molecules in water-in-oil emulsion," Electrophoresis, vol. 22, pp. 289-293, (2001).

Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).

Hidenori Nagai et al., "Development of a Microchamber Array for Picoliter PCR," Analytical Chemistry, vol. 73, No. 5, pp. 1043-1047, Mar. 1, 2001.

Christopher B. Price, "Regular Review Point of Care Testing," BMJ, vol. 322, May 26, 2001.

3M Specialty Materials, "3M Fluorinert Electronic Liquid FC-3283," product information guide, issued Aug. 2001.

Ivonne Schneegaβ et al., "Miniaturized flow-through PCR with different template types in a silicon chip thermocycler," Lab on a Chip, vol. 1, pp. 42-49, (2001).

Randla M. Hill, "Silicone surfactants—new developments," Current Opinion in Colloid & Interface Science 7, pp. 255-261, (2002).

Richard M. Cawthon, "Telomere measurement by quantitative PCR," Nucleic Acids Research, vol. 30, No. 10, pp. 1-6, (2002).

Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).

Shelley L. Anna et al., "Formation of dispersions using "flow focusing" in microchannels," Applied Physics Letters, vol. 82, No. 3, Jan. 20, 2003.

Goldschmidt GMBH, "Abil® EM 90 Emulsifier for the formulation of cosmetic W/O creams and lotions," degussa. creating essentials brochure, pp. 1-7, May 2003.

Purnendu K. Dasgupta et al., "Light emitting diode-based detectors Absorbance, fluorescence and spectroelectrochemical measurements in a planar flow-through cell," Analytica Chimica Acta 500, pp. 337-364, (2003).

R. G. Rutledge et al., "Mathematics of quantitative kinetic PCR and the application of standard curves," Nucleic Acids Research, vol. 31, No. 16, pp. 1-6, (2003).

Chunming Ding et al., "Direct molecular haplotyping of long-range genomic DNA with M1-PCR," PNAS, vol. 100, No. 13, pp. 7449-7453, Jun. 24, 2003.

(56) References Cited

OTHER PUBLICATIONS

Devin Dressman et al., "Transforming single DNA molecules into fluorescent magnetic particles for detection and enumeration of genetic variations," PNAS, vol. 100, No. 15, Jul. 22, 2003.

Ulf Landegren et al., "Padlock and proximity probes for in situ and array-based analyses: tools for the post-genomic era," Comp. Funct. Genom, vol. 4, pp. 525-530, (2003).

Gudrun Pohl et al., "Principle and applications of digital PCR" review, www.future-drugs.com, Expert Rev. Mol. Diagn. 4(1), pp. 41-47, (2004).

Groff M. Schroeder et al., "Introduction to Flow Cytometry" version 5.1, 182 pgs. (2004).

Stéphane Swillens et al., "Instant evaluation of the absolute initial number of cDNA copies from a single real-time PCR curve," Nucleic Acids Research, vol. 32, No. 6, pp. 1-6, (2004).

Mats Gullberg et al., "Cytokine detection by antibody-based proximity ligation," PNAS, vol. 101, No. 22, pp. 8420-8424, Jun. 1, 2004.

Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.

R. G. Rutledge, "Sigmoidal curve-fitting redefines quantitative real-time PCR with the prospective of developing automated high-throughput applications," Nucleic Acids Research. vol. 32, No. 22, pp. 1-8, (2004).

L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.

Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.

James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).

Piotr Garstecki et al., "Mechanism for Flow-Rate Controlled Breakup in Confined Geometries: A Route to Monodisperse Emulsions," Physical Review Letters, 164501, pp. 164501-1 — 164501-4, Apr. 29, 2005.

Anna Musyanovych et al., "Miniemulsion Droplets as Single Molecule Nanoreactors for Polymerase Chain Reaction," Biomacromolecules, vol. 6, No. 4, pp. 1824-1828, (2005).

Max Chabert et al., "Droplet fusion by alternating current (AC) field electrocoalescence in microchannels," Electrophoresis, vol. 26, pp. 3706-3715, (2005).

Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).

Marcel Margulies et al., "Genome sequencing in microfabricated high-density picolitre reactors," Nature, vol. 437, 51 pgs., Sep. 15, 2005.

Kristofer J. Thurecht et al., "Investigation of spontaneous microemulsion formation in supercritical carbon dioxide using high-pressure NMR," Journal of Supercritical Fluids, vol. 38, pp. 111-118, (2006).

Toshko Zhelev et al., "Heat Integration in Micro-Fluidic Devices," 16th European Symposium on Computer Aided Process Engineering and 9th International Symposium on Process Systems Engineering, pp. 1863-1868 published by Elsevier B.V. (2006).

Piotr Garstecki et al., "Formation of droplets and bubbles in a microfluidic T-junction — scaling and mechanism of break-up," Lab on a Chip, vol. 6, pp. 437-446, (2006).

Darren R. Link et al., "Electric Control of Droplets in Microfluidic Devices," Angewandte Chemie Int. Ed., vol. 45, pp. 2556-2560, (2006).

Peter Fielden et al., "Micro-Droplet Technology for High Throughout Systems and Methods," 1 pg., Mar. 8, 2006.

David Emerson et al., "Microfluidic Modelling Activities at C3M," Centre for Microfluidics & Microsystems Modelling, Daresbury Laboratory, pp. 1-26, May 15, 2006.

Richard Williams et al., "Amplification of complex gene libraries by emulsion PCR," Nature Methods, vol. 3, No. 7, pp. 545-550, Jul. 2006.

John H. Leamon et al., "Overview: methods and applications for droplet compartmentalization of biology," Nature Methods, vol. 3, No. 7, pp. 541-543, Jul. 2006.

Andrew D. Griffiths et al., "Miniaturising the laboratory in emulsion droplets," Trends in Biotechnology, vol. 24, No. 9, pp. 395-402, Jul. 14, 2006.

Jian-Bing Fan et al., "Highly parallel genomic assays," Nature Reviews/Genetics, vol. 7, pp. 632-644, Aug. 2006.

Jonas Jarvius et al., "Digital quantification using amplified single-molecule detection," Nature Methods, vol. 3, No. 9, pp. 15 pgs, Sep. 2006.

Kan Liu et al., "Droplet-based synthetic method using microflow focusing and droplet fusion," Microfluid Nanfluid, vol. 3, pp. 239-243, (2007), published online Sep. 22, 2006.

Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.

Kristofer J. Thurecht et al., "Kinetics of Enzymatic Ring-Opening Polymerization of □-Caprolactone in Supercritical Carbon Dioxide," Macromolecules, vol. 39, pp. 7967-7972, (2006).

Machiko Hori et al., "Uniform amplification of multiple DNAs by emulsion PCR," Biochemical and Biophysical Research Communications, vol. 352, pp. 323-328, (2007).

Frank Diehl et al., "Digital quantification of mutant DNA in cancer patients," Current Opinion in Oncology, vol. 19, pp. 36-42, (2007).

Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).

S. Mohr et al., "Numerical and experimental study of a droplet-based PCR chip," Microfluid Nanofluid, vol. 3, pp. 611-621, (2007).

Sigrun M. Gustafsdottir et al., "In vitro analysis of DNA-protein interactions by proximity ligation," PNAS, vol. 104, No. 9, pp. 3067-3072, Feb. 27, 2007.

Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.

Charles N. Baroud et al., "Thermocapillary valve for droplet production and sorting," Physical Review E 75, 046302, pp. 046302-1 — 046302-5, Apr. 5, 2007.

Qinyu Ge et al., "Emulsion PCR-based method to detect Y chromosome microdeletions," Analytical Biochemistry, vol. 367, pp. 173-178, May 10, 2007.

Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.

Y. M. Dennis Lo et al., "Digital PCR for the molecular detection of fetal chromosomal aneuploidy," PNAS, vol. 104, No. 32, pp. 13116-13121, Aug. 7, 2007.

Dayong Jin et al., "Practical Time-Gated Luminescence Flow Cytometry. II: Experimental Evaluation Using UV LED Excitation," Cytometry Part A • 71A, pp. 797-808, Aug. 24, 2007.

Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.

Nathan Blow, "PCR's next frontier," Nature Methods, vol. 4, No. 10, pp. 869-875, Oct. 2007.

Nicole Pamme, "continuous flow separations in microfluidic devices," Lab on a Chip, vol. 7, pp. 1644-1659, Nov. 2, 2007.

N. Reginald Beer et al., "On-Chip, Real-Time, Single-Copy Polymerase Chain Reaction in Picoliter Droplets," Analytical Chemistry, vol. 79, No. 22, pp. 8471-8475, Nov. 15, 2007.

(56) References Cited

OTHER PUBLICATIONS

Yuejun Zhao et al., "Microparticle Concentration and Separation by Traveling-Wave Dielectrophoresis (twDEP) for Digital Microfluidics," Journal of Microelectromechanical Systems, vol., 16, No. 6, pp. 1472-1481, Dec. 2007.
Sigma-Aldrich, "Synthesis of Mesoporous Materials," Material Matters, 3.1, 17, (2008).
Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Shia-Yen Teh et al., "Droplet microfluidics," Lab on a Chip, vol. 8, pp. 198-220, Jan. 11, 2008.
Chloroform (Phenomenex), Solvent Miscibility Table, Internet Archive WayBackMachine, 3 pgs., Feb. 1, 2008.
N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Palani Kumaresan et al., "High-Throughput Single Copy DNA Amplification and Cell Analysis in Engineered Nanoliter Droplets," Analytical Chemistry, 17 pgs., Apr. 15, 2008.
Somil C. Mehta et al., "Mechanism of Stabilization of Silicone Oil — Water Emulsions Using Hybrid Siloxane Polymers," Langmuir, vol. 24, No. 9, pp. 4558-4563, Mar. 26, 2008.
Rhutesh K. Shah et al., "Polymers fit for function Making emulsions drop by drop," Materials Today, vol. 11, No. 4, pp. 18-27, Apr. 2008.
Mohamed Abdelgawad et al., "All-terrain droplet actuation," Lab on a Chip, vol. 8, pp. 672-677, Apr. 2, 2008.
Lung-Hsin Hung et al., "Rapid microfabrication of solvent-resistant biocompatible microfluidic devices," Lab on a Chip, vol. 8, pp. 983-987, Apr. 8, 2008.
Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.
Vivienne N. Luk et al., "Pluronic Additives: A Solution to Sticky Problems in Digital Microfluidics," Langmuir, vol. 24, No. 12, pp. 6382-6289, May 16, 2008.
Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.
Simant Dube et al., "Mathematical Analysis of Copy Number Variation in a DNA Sample Using Digital PCR on a Nanofluidic Device," PLoS ONE, vol. 3, Issue 8, pp. 1-9, Aug. 6, 2008.
Jian Qin et al., "Studying copy number variations using a nanofluidic platform," Nucleic Acids Research, vol. 36, No. 18, pp. 1-8, Aug. 18, 2008.
C. Holtze et al., "Biocompatible surfactants for water-in-fluorocarbon emulsions," Lab on a Chip, vol. 8, pp. 1632-1639, Sep. 2, 2008.
Margaret Macris Kiss et al., "High-Throughput Quantitative Polymerase Chain Reaction in Picoliter Droplets," Analytical Chemistry, 8 pgs., downloaded Nov. 17, 2008.
Bernhard G. Zimmermann et al., "Digital PCR: a powerful new tool for noninvasive prenatal diagnosis?," Prenatal Diagnosis, vol. 28 pp. 1087-1093, Nov. 10, 2008.
Avishay Bransky et al., "A microfluidic droplet generator based on a piezoelectric actuator," Lab on a Chip, vol. 9, pp. 516-520, Nov. 20, 2008.
David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Neil Reginald Beer et al., "Monodisperse droplet generation and rapid trapping for single molecule detection and reaction kinetics measurement," Lab on a Chip, vol. 9, pp. 841-844, Dec. 5, 2008.
Richard M. Cawthon, "Telomere length measurement by a novel monochrome multiplex quantitative PCR method," Nucleic Acids Research, vol. 37, No. 3, pp. 1-7, (2009).
Anthony J. O'Lenick, Jr., "Silicone Emulsions and Surfactants — A Review," Silicone Spectator, Silitech LLC, May, 2009 (original published May 2000).
Adam R. Abate et al., "Functionalized glass coating for PDMS microfluidic devices," Lab on a Chip Technology: Fabrication and Microfluidics, 11 pgs., (2009).
Chia-Hung Chen et al., "Janus Particles Templated from Double Emulsion Droplets Generated Using Microfluidics," Langmuir, vol. 29, No. 8, pp. 4320-4323, Mar. 18, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Linas Mazutis et al., "A fast and efficient microfluidic system for highly selective one-to-one droplet fusion," Lab on a Chip, vol. 9, pp. 2665-2672, Jun. 12, 2009.
Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Frank McCaughan et al., "Single-molecule genomics," Journal of Pathology, vol. 220, pp. 297-306, Nov. 19, 2009.
Suzanne Weaver et al., "Taking qPCR to a higher level: Analysis of CNV reveals the power of high throughput qPCR to enhance quantitative resolution," Methods, vol. 50, pp. 271-276, Jan. 15, 2010.
Amelia L. Markey et al., "High-throughput droplet PCR," Methods, vol. 50, pp. 277-281, Feb. 2, 2010.
Yoon Sung Nam et al., "Nanosized Emulsions Stabilized by Semi-solid Polymer Interphase," Langmuir, ACS Publications, Jul. 23, 2010.
Tatjana Schütze et al., "A streamlined protocol for emulsion polymerase chain reaction and subsequent purification," Analytical Biochemistry, vol. 410, pp. 155-157, Nov. 25, 2010.
Somanath Bhat et al., "Effect of sustained elevated temperature prior to amplification on template copy number estimation using digital polymerase chain reaction," Analyst, vol. 136, pp. 724-732, (2011).
James G. Wetmur, et al., "Linking Emulsion PCR Haplotype Analysis," PCR Protocols, Methods in Molecular Biology, vol. 687, pp. 165-175, (2011).
Paul Vulto et al., "Phaseguides: a paradigm shift in microfluidic priming and emptying," Lab on a Chip, vol. 11, No. 9, pp. 1561-1700, May 7, 2011.
Thinxxs Microtechnology AG, "Emerald Biosystems: Protein Crystallization," 1 pg., downloaded Mar. 8, 2011.
Qun Zhong et al., "Multiplex digital PCR: breaking the one target per color barrier of quantitative PCR," Lab on a Chip, vol. 11, pp. 2167-2174, (2011).
Burcu Kekevi et al., Synthesis and Characterization of Silicone-Based Surfactants as Anti-Foaming Agents, J. Surfact Deterg (2012), vol. 15, pp. 73-81, published online Jul. 7, 2011.
Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Nicole L. Solimini et al., "Recurrent Hemizygous Deletions in Cancers May Optimize Proliferative Potential," Science, vol. 337, pp. 104-109, Jul. 6, 2012.
Labsmith, "Microfluid Components" webpage, downloaded Jul. 11, 2012.
Labsmith, "CapTite™ Microfluidic Interconnects" webpage, downloaded Jul. 11, 2012.
Nathan A. Tanner et al., "Simultaneous multiple target detection in real-time loop-mediated isothermal amplification," BioTechniques, vol. 53, pp. 8-19, Aug. 2012.

* cited by examiner

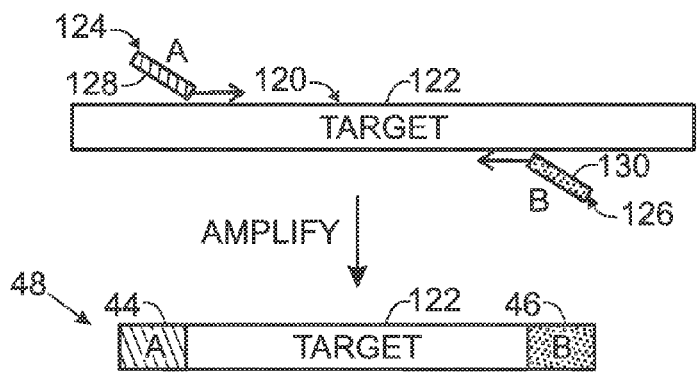
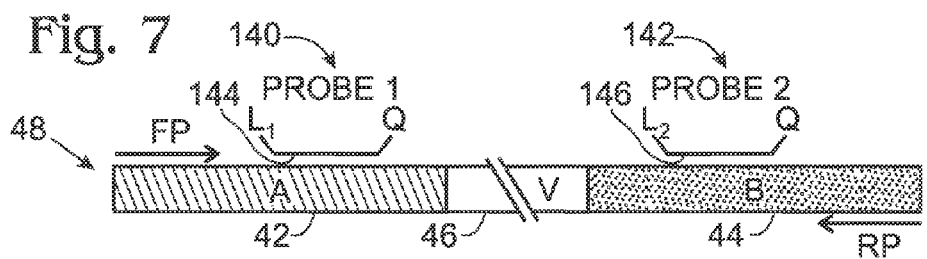
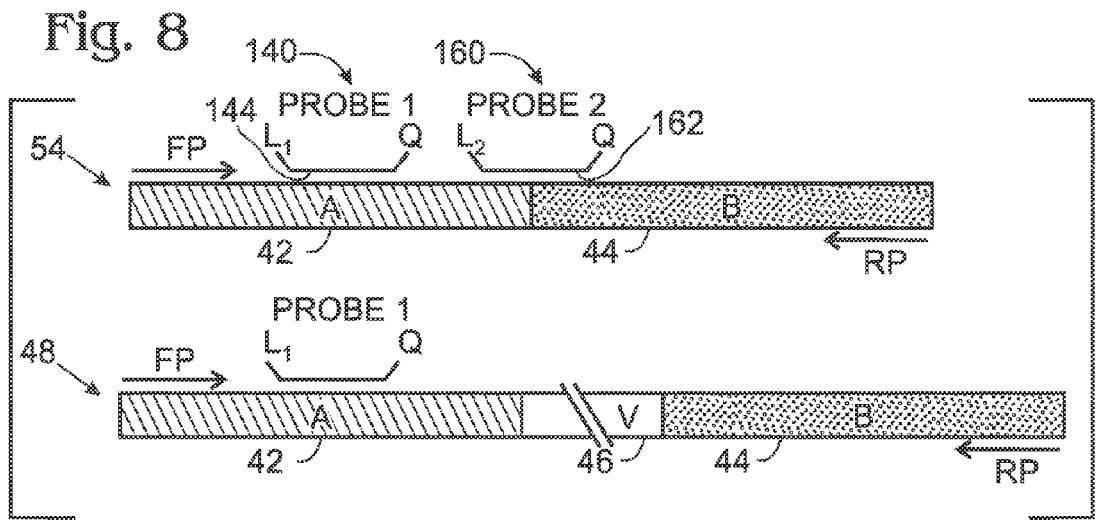

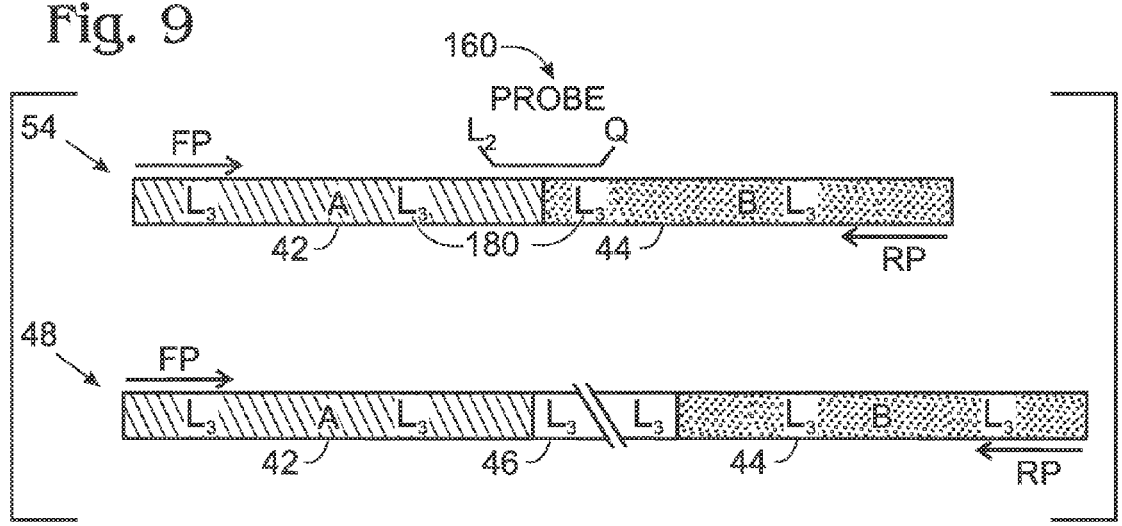

LIBRARY CHARACTERIZATION BY DIGITAL ASSAY

CROSS-REFERENCE TO PRIORITY APPLICATIONS

This application is based upon and claims the benefit under 35 U.S.C. §119(e) of U.S. Provisional Patent Application Ser. No. 61/513,474, filed Jul. 29, 2011; and U.S. Provisional Patent Application Ser. No. 61/601,514, filed Feb. 21, 2012. Each of these priority applications is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; U.S. patent application Ser. No. 13/251,016, filed Sep. 30, 2011; U.S. patent application Ser. No. 13/548,062, filed Jul. 12, 2012; and Joseph R. Lakowicz, PRINCIPLES OF FLUORESCENCE SPECTROSCOPY ($2^{nd}$ Ed. 1999).

INTRODUCTION

DNA sequencing determines the order of nucleotide bases in a DNA molecule. The ability to obtain sequence information quickly is crucial to many fields, such as biological research, clinical diagnostics, pharmacogenomics, forensics, and environmental studies. Due to the demand for improved sequencing technologies, the speed of sequence acquisition has increased dramatically over the past several decades.

The predominant first-generation sequencing technology is a chain-termination method developed by Frederick Sanger in 1977. The Sanger method performs a sequencing reaction for each sample in a separate reaction vessel and resolves reaction products according to size by electrophoresis in a gel or capillary. The ability to scale up the Sanger method for a very large number of samples is limited by the space and individual manipulations needed for each sample (e.g., transferring the reacted sample from its reaction vessel to a gel or capillary).

Next-generation sequencing technologies, such as pyrosequencing (Roche Diagnostics), sequencing by synthesis (Illumina), and sequencing by oligonucleotide ligation and detection (Life Technologies), overcome the major limitations of the first-generation approach. Sequencing reactions can be performed in parallel with a very large number of different samples (templates) immobilized in an array in the same flow cell. The density of samples per unit area can be very high, and the total number of samples can be increased by enlarging the array. The samples can be exposed to a series of sequencing reagents in parallel in a shared fluid volume inside the flow cell. Also, the samples in the array can be monitored with a camera to record sequence data from all of the samples in real time as the sequencing reactions proceed in parallel with cyclical exposure to reagents passing through the flow cell. Next-generation sequencing technologies are responsible for a dramatic increase in sequencing speed—orders of magnitude—over the past decade.

First-generation methods generally utilize conventional libraries to produce a sufficient amount of each template for sequencing. A first-generation library may be composed of a collection of DNA fragments inserted into a vector, such as a plasmid or a bacteriophage vector. Each inserted fragment is cloned by placing the vector in a suitable host organism, such as a bacterium, which can replicate the vector and the fragment to make many clonal copies. In contrast, next-generation technologies increase throughput dramatically by providing the capability to sequence in vitro libraries constructed exclusively in vitro by the action of one or more enzymes. In vitro libraries do not contain or need a vector for replication in vivo because each fragment is cloned by amplification in vitro, such as through the polymerase chain reaction (PCR). Accordingly, in vitro libraries can be constructed from very small amounts of nucleic acid and permit sequencing of rare species (e.g., rare mutations) that occur at a very low frequency in a sample.

Next-generation technologies currently on the market rely on in vitro libraries having a particular construction. The various fragments to be sequenced are each flanked by adapters to form library members. The adapters provide primer binding sites for clonal amplification of each library member on a support, such as on a flat surface or beads. The adapters can introduce binding sites that enable amplification of all members of the library with the same primer or pair of adapter-specific primers. Also, one or both of the adapters can provide a binding site for a sequencing primer. Furthermore, an adapter can introduce a library-specific index sequence that permits members of different libraries to be pooled and sequenced together in the same flow cell, without losing track of the library of origin for each member.

A set of libraries can be constructed in parallel, such as in different wells of a multi-well plate, from different nucleic acid samples. However, despite the best efforts to achieve uniform reaction conditions among the wells, the concentration and quality of the libraries can vary widely.

SUMMARY

The present disclosure provides methods of characterizing a nucleic acid library by digital assay.

BRIEF DESCRIPTION OF THE DRAWINGS

FIG. 6 is yet another exemplary reaction diagram illustrating yet another exemplary approach for constructing members of the library of FIG. 1, in accordance with aspects of the present disclosure.

FIG. 7 is a schematic representation of exemplary amplification primers and probes for use in a digital amplification assay to quantify library members containing both of the different adapters of FIG. 1, in accordance with aspects of the present disclosure.

FIG. 8 is a schematic representation of exemplary amplification primers and probes for use in a digital amplification assay to quantify empty and filled library members, in accordance with aspects of the present disclosure.

FIG. 9 is a schematic representation of exemplary amplification primers, a probe, and an intercalating reporter for use in a digital amplification assay to quantify empty and filled library members, in accordance with aspects of the present disclosure.

DETAILED DESCRIPTION

Figure 1:
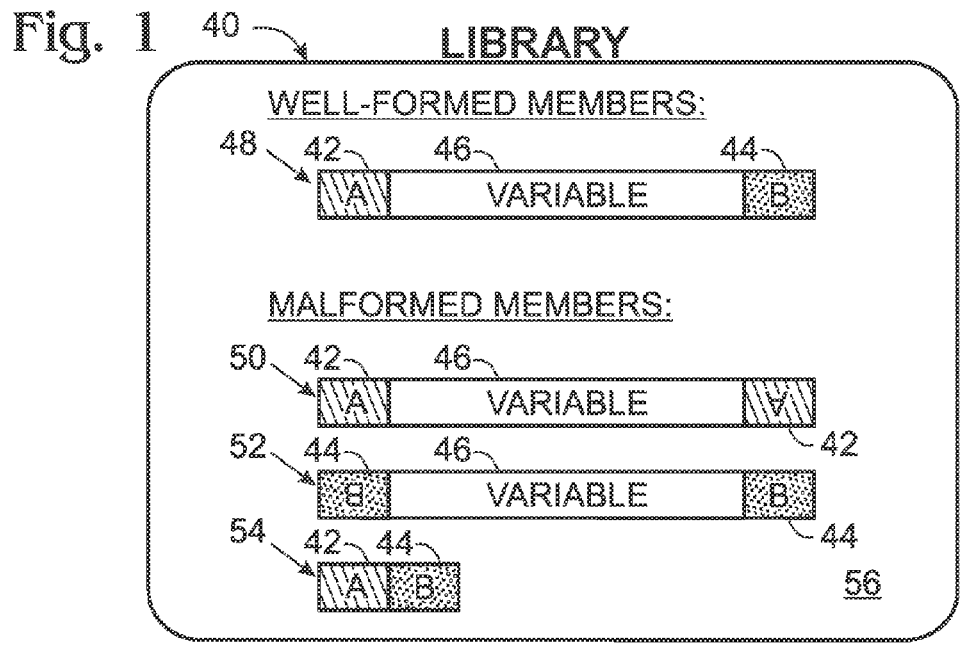
FIG. 1 is schematic representation of an exemplary library that may be characterized according to the present disclosure, with the library being constructed with a pair of different adapters and including well-formed and malformed members, in accordance with aspects of the present disclosure.

The present disclosure provides methods of characterizing a nucleic acid library by digital assay.

An exemplary method of library characterization is provided. In the method, a nucleic acid library may be obtained. The library may include members each having a first adapter region and a second adapter region. At least a subset of the members may have an insert disposed between the first and second adapter regions. At least a portion of the library may be divided into partitions. A digital assay may be performed on the partitions with an adapter region probe to generate data indicating whether a library member is present in each partition. A characteristic of the library may be determined based on the data.

Another exemplary method of library characterization is provided. In the method, a nucleic acid library may be obtained. The library may include members each having a first constant region and a second constant region. At least a subset of the members may have a variable region disposed between the first and second constant regions.

Droplets containing members of the library at limiting dilution may be formed. Members of the library may be amplified in the droplets using a primer for each constant region. Amplification data may be collected from a constant region probe in the droplets. A level of members of the library may be determined based on the amplification data.

Library characterization before sequencing can be problematic. Only properly formed library members containing both adapters in the correct relative orientation produce clonal populations that can be interrogated reliably by sequencing. Malformed members in the library, such as members flanked by two copies of only one of the adapters, can be difficult to distinguish from those that are well-formed. However, the malformed members generally cannot be amplified on a support, a prerequisite to sequence acquisition, or do not have a binding site for the sequencing primer, or both. As a result, malformed members can take up space and consume reagents and can reduce the amount of useful sequence information produced by a next-generation sequencing run, in direct proportion to the fraction of malformed members in the library.

The methods for library characterization disclosed herein may have numerous advantages over other approaches. These advantages may include the ability to obtain more information about library quality (e.g., quantification of both well-formed and malformed library members, quantification of empty and filled library members, qualitative indication of library complexity, or the like), fewer sequencing runs wasted, increased speed, less library material used for analysis, and/or more accurate concentration estimates, among others. Also, the ability to quantify well-formed library members enhances significantly the chance of optimal loading of libraries prior to sequencing.

Further aspects of the present disclosure are presented in the following sections: (I) library overview, (II) methods of library characterization, (III) library construction, (IV) primers and probes, and (V) examples.

I. Library Overview

FIG. 1 shows an exemplary in vitro, nucleic acid library 40 that may be characterized according to the methods disclosed herein. Members of the library each may include one or more adapter regions 42, 44 ("A", "B"), which also or alternatively may be termed adapters or constant regions, and an insert 46, which also or alternatively may be termed a variable region and/or a variable insert. Each insert may be disposed between adapter regions 42, 44, such that the insert is flanked by the adapter regions (i.e., attached at each opposing end to an adapter region). Inserts 46 of the library may be supplied by fragments, which may be attached at each end to an adapter that provides one of the adapter/constant regions.

Inserts 46 of the library are of interest for sequencing analysis and may vary substantially in sequence among members of the library. For example, the inserts may provide a variable region corresponding to a diverse collection of fragments generated from a source material for a shotgun sequencing strategy. However, in some cases, such as in a deep-sequencing approach that looks for rare mutations, the inserts may have a low frequency of variability. In any event, the adapter regions provide binding sites for primers and/or probes at the ends of each well-formed member 48 of the library Adapters that provide adapter regions 42, 44 may be attached to inserts 46 and to each other during library construction in various combinations to create desired, well-formed members 48 (only one is shown in FIG. 1) and malformed members, such as members 50-54. The well-formed members have the correct structure, with a different adapter region 42 or 44 attached to each end of the insert (i.e., "A" at one end and "B" at the other end), and in the correct relative orientation of the adapter regions. The well-formed library members, due to the presence of both adapter regions 42, 44 in the correct relative orientation, are capable of being amplified clonally on a solid support with a pair of adapter primers as a preparatory step in a sequencing protocol.

Malformed members of the library are formed incorrectly and may have a variety of different structures, such as those shown in FIG. 1. The malformed members illustrated here are each capable of being amplified in solution, in the presence of the same pair of adapter primers that can amplify well-formed library members.

Malformed members 50, 52 have a copy of the same adapter region attached to each end of the insert (i.e., a copy of "A" at both ends or a copy of "B" at both ends). The copies may be arranged as inverted repeats (i.e., rotated 180 degrees relative to one another in the drawing), which is represented in FIG. 1 by the rightward "A" copy and the leftward "B" copy being upside down and backwards in members 50 and 52, respectively. Furthermore, an empty library member 54 may be created if the different adapters attach directly to each other in the correct relative orientation but with no intervening insert. In any event, malformed members generally do not yield any useful sequencing data. For example, malformed members may not be amplifiable clonally on a primer-coated support (e.g., a primer-coated bead). Alternatively, or in addition, malformed members may lack the binding site for a sequencing primer used for the well-formed members, or may have more than one instance of the binding site, such that sequence reads are superimposed on one other. Furthermore, malformed library members may not carry a sequence of interest (e.g., empty member 54). The proportion of malformed members in a library can vary substantially based, for example, on the integrity and concentration of the DNA fragments that provide inserts 46, the ratio of adapters to insert fragments used for ligation, the presence of inhibitors or other contaminants, and the like.

Inserts 46 may be formed with fragments of DNA, such as pieces of genomic DNA, mitochondrial DNA, chloroplast DNA, cDNA, or the like, from any suitable source. The fragments may have any suitable length, such as about 10 to 10,000, or 20 to 2,000 nucleotides, among others. The fragments may or may not be size-selected before attachment to the adapters. Fragments may be generated from a source nucleic acid material by any suitable approach, such as shearing, chemical digestion, enzymatic digestion, amplification with one or more primers, reverse transcription, end-polishing, or any combination thereof, among others. The fragments may have flush or overhanging ends, and may be at least predominantly double-stranded or single-stranded.

Each adapter (or adapter region) may have any suitable structure before and/or after attachment to inserts. The adapter before attachment may include a nucleic acid or nucleic acid analog. Each adapter may be formed by one or more oligonucleotide strands each having any suitable length, such as at least about 6, 8, 10, 15, 20, 30, or 40 nucleotides, among others, and/or less than about 200, 100, 75, or 50 nucleotides, among others. The adapter may be provided by one or more oligonucleotides that are chemically synthesized in vitro. The adapter may be configured to be attached to inserts at only one of its two ends. In some cases, the adapter may be partially or completely single-stranded before attachment to inserts, such as if the adapter is provided by a primer that attaches to inserts via primer extension.

Library 40 may include any suitable medium in which library members (such as members 48-54) are disposed. The medium may be an aqueous phase 56, which may include salt, buffer, surfactant, at least one enzyme (e.g., ligase, polymerase, etc.), unligated adapters, one or more primers, one or more probes, or any combination thereof, among others.

II. Methods of Library Characterization

This section provides an overview of exemplary methods of characterizing a library containing inserts attached to adapters. The method steps disclosed in this section and elsewhere in the present disclosure may be performed in any suitable combination, in any suitable order, and any suitable number of times.

Figure 2:
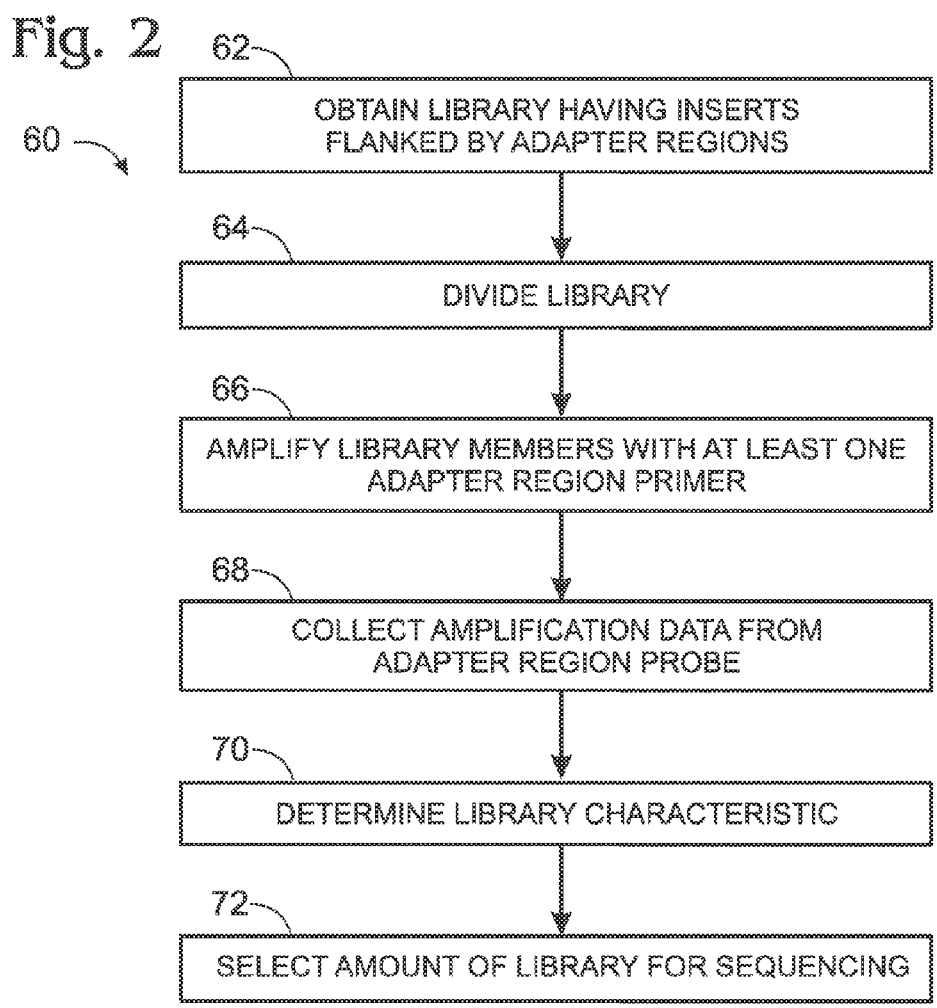
FIG. 2 is a flowchart of selected aspects of an exemplary method of characterizing the library of FIG. 1, in accordance with aspects of the present disclosure.

FIG. 2 shows a flowchart of selected aspects of an exemplary method 60 of characterizing library 40 of FIG. 1 before the library is sequenced. Method 60 may, for example, be performed before sequencing to determine how much of the library to use in a sequencing protocol (e.g., to prevent underloading or overloading) and/or to determine whether or not the library is of sufficient quality for the sequencing protocol. Library characterization also or alternatively may be performed for any other purpose.

Method 60 may be used to perform a digital assay on the library members. The digital assay relies on the ability to detect the presence of a single library member in individual partitions of the library. In an exemplary digital assay, at least a portion of a library is separated into a set of partitions, which may be of equal volume. The library may be separated at limiting dilution, with some of the partitions containing no library members and others containing only one library member. If the library members are distributed randomly among the partitions, some partitions should contain no members, others only one member, and, if the number of partitions is large enough, still others should contain two members, three members, and even higher numbers of members. The probability of finding exactly 0, 1, 2, 3, or more library members in a partition, based on a given average concentration of members in the partitions, is described by Poisson statistics. Conversely, the concentration of the members in the partitions (and in the library) may be determined from the probability of finding a given number of library members in a partition.

Estimates of the probability of finding no library members and of finding one or more library members may be measured in the digital assay. Each partition can be tested to determine whether the partition is a positive partition that contains at least one library member, or is a negative partition that contains no library members. The probability of finding no library members in a partition can be approximated by the fraction of partitions tested that are negative (the "negative fraction"), and the probability of finding at least one library member by the fraction of partitions tested that are positive (the "positive fraction"). The positive fraction (or, equivalently, the negative fraction) then may be utilized in a Poisson equation to determine the concentration of library members in the partitions.

Digital amplification assays may rely on amplification of templates (e.g., templates provided by library members) in partitions to enable detection of a single library member. Amplification may, for example, be conducted via PCR, to achieve a digital PCR assay. Amplification of the library members can be detected optically from a luminescent reporter included in the reaction. In particular, the reporter can include a luminophore (e.g., a fluorophore) that emits light (luminesces) according to whether or not a library member has been amplified in a given partition. The luminophore may emit light in response to illumination with suitable excitation light.

A digital PCR assay can be multiplexed to permit detection of two or more different types of templates or targets (e.g., different types of library members, such as well-formed and malformed members, empty and filled/total members, etc.) within each partition. Amplification of the different types of library members can be distinguished by utilizing target-specific reporters (e.g., probes) that are optically distinguishable. For example, the reporters may include distinct luminophores producing distinguishable luminescence that can be detected with different detection regimes, such as different excitation and/or detection wavelengths or wavebands and/or different detection times after excitation, among others. In some cases, different target-specific reporters can be distinguished based on intensity differences measured in the same detection channel.

In method 60, a library for characterization may be obtained, indicated at 62. The library may include members each having at least one adapter region or a pair of different adapter regions, which may be constant regions. Library members also may include inserts and/or a variable region, with at least some of the inserts each being attached at one end to a first adapter region and at the other end to a second adapter region. The library may be obtained by constructing the library or may be received from a third party. The library may be constructed, at least in part, by attaching adapters to fragments (e.g., a diverse collection of fragments), such as in the presence of a ligase enzyme. After attachment of adapters, the library may be pre-amplified any suitable amount before the library is partitioned, to increase the quantity of library material available for quantification, quality analysis, and/or sequencing. Alternatively, after attachment of adapters, the library may be partitioned without prior amplification.

In some cases, first and second adapter regions that opposingly flank inserts of the library may be provided by a compound adapter that is attached to both ends of the inserts. The compound adapter may have a double-stranded region and a pair of single-stranded regions, with the single-stranded regions each provided by a different strand and extending from the same end of the double-stranded region. One strand of the compound adapter may provide the first adapter region and a second strand of the compound adapter may provide the second adapter region of library members.

In other cases, the library may be constructed by contacting fragments with a first adapter and a second adapter. The first and second adapters may be discrete from each other and not substantially base-paired to each other.

In still other cases, the library may be constructed by linking adapters to inserts by primer-based amplification. For example, a pair of tailed primers may be used to generate an insert from a template, with the primers providing the first and second adapters.

Library construction also may include any suitable supplementary reactions or processes, such as end-filling, nick repair, conversion to single-stranded form, purification, size selection, or the like. Further aspects of library construction are described below in Section III.

At least a portion of the library may be divided into partitions, indicated at 64. Partitions of the library may be distributed to a plurality of reaction sites. The reaction sites may be movable or fixed relative to one another. The reaction sites may be formed by discrete fluid volumes isolated from one another by one or more walls and/or by a separating fluid (e.g., a continuous phase of an emulsion). Alternatively, the reaction sites may be provided by a continuous surface (such as reaction sites arrayed on the surface of a chip) or beads, among others. The partitions may be distributed at a limiting dilution of members of the library, meaning that a plurality of the reaction sites do not receive a library member and/or such that a plurality of the reaction sites receive only one library member.

In some embodiments, at least part of the library may be partitioned into fluid volumes that serve as reaction sites. The fluid volumes may be isolated from one another by a fluid phase, such as a continuous phase of an emulsion, by a solid phase, such as at least one wall of a container, or a combination thereof, among others. In some embodiments, the fluid volumes may be droplets disposed in a continuous phase, such that the droplets and the continuous phase collectively form an emulsion.

The fluid volumes may be formed by any suitable procedure, in any suitable manner, and with any suitable properties. For example, the fluid volumes may be formed with a fluid dispenser, such as a pipet, with a droplet generator, by forceful mixing (e.g., shaking, stirring, sonication, etc.), and/or the like. Accordingly, the fluid volumes may be formed serially, in parallel, or in batch. The fluid volumes may be of substantially uniform volume or may have different volumes. Exemplary fluid volumes having the same volume are monodisperse droplets. Exemplary volumes for the fluid volumes include an average volume of less than about 100, 10 or 1 µL, less than about 100, 10, or 1 nL, or less than about 100, 10, or 1 pL, among others.

The fluid volumes, when formed, may be competent for performance of one or more reactions in the fluid volumes, such as amplification of library members (and, optionally, associated probe degradation). Alternatively, one or more reagents may be added to the fluid volumes after they are formed to render them competent for reaction. The reagents may be added by any suitable mechanism, such as a fluid dispenser, fusion of droplets, or the like.

Library members may be amplified, indicated at 66, at the reaction sites (e.g., in the fluid volumes). For example, library members may be amplified with a primer for each adapter region flanking the insert. In some cases, a pair of primers may be used, with one of the primers binding to the first adapter region attached at one end of the inserts and the other primer binding to the second adapter region attached at the other end of the inserts. In other examples, a single primer may be suitable for amplification, if the first and second adapter regions share a sequence that allows the same primer to bind to both adapter regions. In any event, amplification may be substantially restricted to constructs that contain a pair of primer binding sites arranged for convergent extension into the insert from binding sites for a pair of primers (see Section IV). For example, if amplification of well-formed member 48 (see FIG. 1) is performed with a forward primer that binds to "A" and a reverse primer that binds to "B," each of malformed members 50-54 also can be amplified. However, other constructs, such as a construct having an insert flanked by a direct (not inverted) repeat of "A" or "B" generally would not amplify with these primers. Additional or other primers may be utilized if these other constructs are to be amplified and detected.

Amplification may be performed by any suitable reactions. For example, amplification may be performed by a polymerase chain reaction. Alternatively, or in addition, amplification may be performed by a ligase chain reaction. In any event, the reaction sites (e.g., fluid volumes) may be thermally cycled to promote amplification.

Amplification may be performed in the presence of one or more labeled reporters. For example, each reaction site (e.g., fluid volume) may include a first labeled probe capable of binding the first adapter region (e.g., adapter A; see FIG. 1) and a second labeled probe capable of binding the second adapter region (e.g., adapter B). Each labeled probe may include a luminophore. For example, the probe may include an energy transfer pair, namely, an energy donor (generally a luminophore) and an energy acceptor. The energy acceptor may be another luminophore or a quencher. The probe may produce a stronger signal when in a degraded form. In other cases, the reporter(s) may include an intercalating luminophore and/or a probe that binds selectively to a junction sequence formed by direct attachment of different adapter regions to each other.

Amplification data may be collected from the reporters, including data collected from an adapter region probe, indicated at 68. The data may be collected from individual reaction sites (e.g., fluid volumes such as droplets). The amplification data may indicate whether a library member (e.g., a particular type of library member) capable of binding the probe is present (and amplified) at a given reaction site. For example, the adapter region probe may be bound selectively by empty library members having no insert. As another example, the adapter region probe may be bound selectively by amplified library members containing adapter A (or adapter B) (see FIG. 1). The data may, for example, be collected by detecting light from individual reaction sites.

Signals may be created that are representative of light detected from each reaction site. The signals may represent data collected in one or more different channels (e.g., in different wavebands (color regimes)) from different luminophores representing amplification of different adapters. Alternatively, or in addition, the signals may represent an aspect of light, such as the intensity of the light, detected in the same channel (e.g., in the same waveband for two different adapter region probes). Further aspects of using the same detection channel for detection of signals from at least a pair of different reporters or probes is described in U.S. patent application Ser. No. 13/548,062, filed Jul. 12, 2012, which is incorporated herein by reference.

Detection may be performed at any suitable time(s). Exemplary times include at the end of an assay (an endpoint assay), when reactions have run to completion and the data no longer are changing, or at some earlier time (a kinetic assay).

At least one characteristic of the library may be determined, indicated at 70, based on the amplification data collected. The characteristic may be an absolute or relative level (e.g., concentration) of library members (e.g., a type of library member). For example, the level may describe library members containing a copy of each different adapter region, with the adapter regions having a defined orientation relative to one another and/or relative to the insert, namely, the relative orientation that permits productive amplification with the forward and reverse, adapter-specific primer(s) utilized at 66. The level determined may include or substantially exclude empty library members having the first adapter region attached to the second adapter region without an intervening fragment. In other examples, the characteristic may be a quality metric of the library, which may, for example, be a measure of library complexity or a measure of the proportion of well-formed members in the library.

In some cases, the amplification data collected at 68 may be processed to determine whether individual reaction sites test positive or negative for amplification of a template or a particular type of template. Each of a plurality of reaction sites may be designated as being amplification-positive or amplification-negative for a first adapter region, for a second adapter region, for a junction produced by direct attachment of the first and second adapter regions to each other, for amplified nucleic acid (e.g., when the reporter is an intercalating luminophore), or any combination thereof, among others. A reaction site may be designated as positive or negative for each of the adapters by comparing, to one or more thresholds or ranges, an adapter signal strength (from an adapter-specific probe) for each adapter, from individual reaction sites. A relative or absolute level of each different adapter region may be determined based on the number and/or fraction of positive or negative reaction sites. The calculation may be based on library members containing both adapters having a Poisson distribution among the reaction sites. The level of library members determined may account for occurrence of an amplifiable first adapter region and an amplifiable second adapter region at the same reaction site by chance, without being linked to one another (see Example 2).

The library characteristic determined may be used to guide library processing, such as to determine whether or not the library is of sufficient quality for sequencing. For example, if the level of empty library members and/or other malformed members is too high, the apparent complexity of well-formed member is too low, or the like, a replacement library may need to be constructed. Alternatively, if the library is of sufficient quality, an amount of the library may be selected for sequencing, indicated at 72, based on the characteristic determined at 70. The amount of library selected may be contacted with a solid support(s) (e.g., a continuous surface or beads) in preparation for clonal amplification of library members on the solid support(s). Individual members of the library may be bound to distinct supports, such as distinct beads (e.g., as in pyrosequencing), or to spaced regions of the same support surface (e.g., as in bridge amplification prior to sequencing by synthesis (Illumina)). For example, the supports/support surface may be pre-attached to many copies of a capture sequence/primer that is complementary to an adapter sequence at the end of each well-formed library member. The supports may be disposed in droplets of an emulsion (e.g., as in pyrosequencing), with each droplet containing, on average, only about one or less well-formed member of the library. The library members may be clonally amplified on the solid support(s) and then may be sequenced by any suitable technology, such as pyrosequencing (Roche Diagnostics), sequencing by oligonucleotide ligation and detection (Life Technologies), sequencing by synthesis (Illumina), or the like.

Knowledge of the library concentration for well-formed members minimizes overloading or under-loading the solid support(s) with library members. With overloading, two or more well-formed library members may be attached to the same support or surface region, resulting later in superimposed sequencing reads, which reduces the amount of useful sequencing information obtained from the run. With underloading, no library members may be attached to the support or surface region, which lies fallow during the sequencing run.

Figure 3:
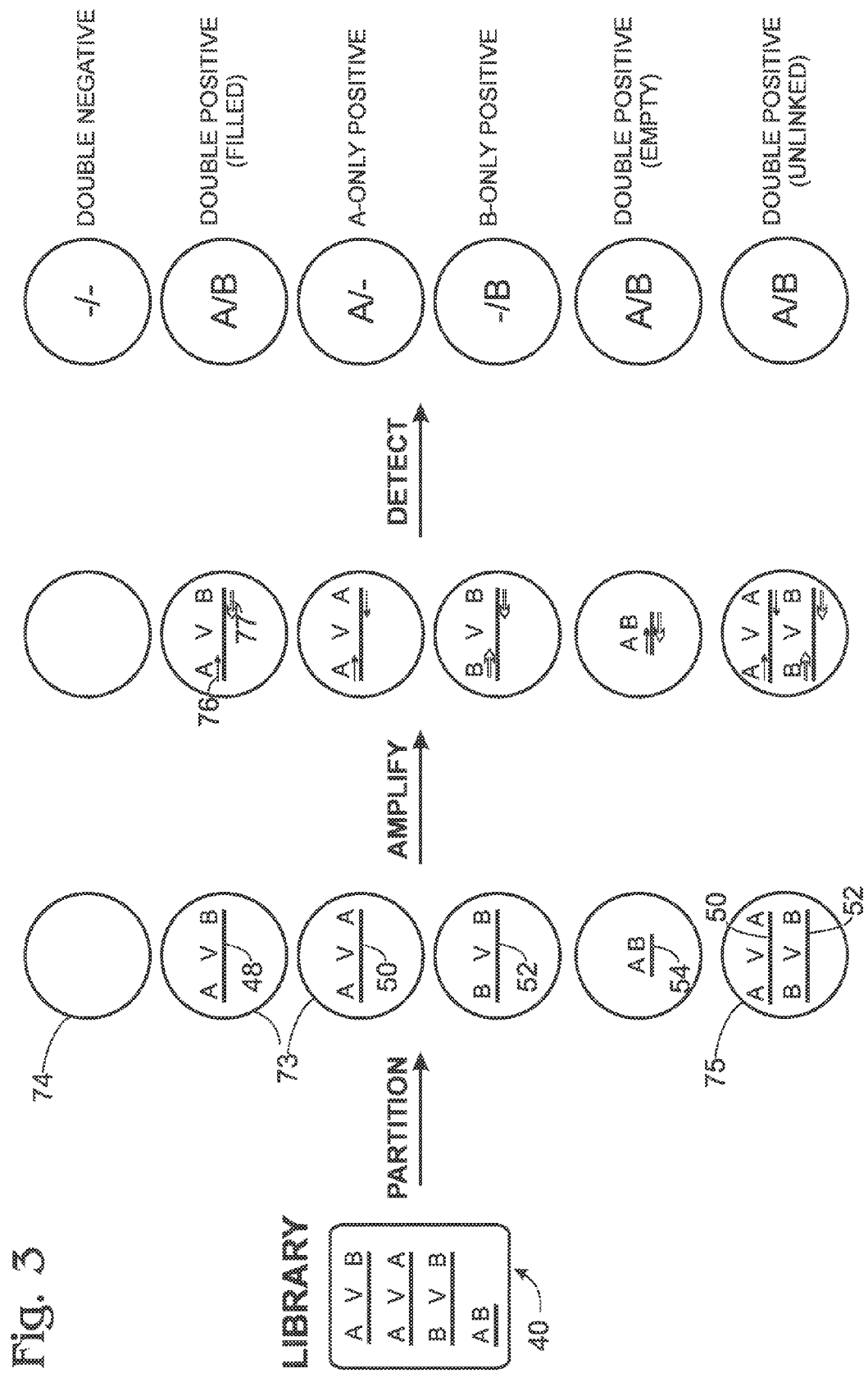
FIG. 3 is a schematic illustration of selected aspects of a library characterization performed according to FIG. 2 and exemplifying amplification data that can be collected from different reaction sites (e.g., discrete fluid volumes, such as distinct droplets), in accordance with aspects of the present disclosure.

FIG. 3 schematically depicts exemplary execution of selected aspects of the method 60 of FIG. 2, and exemplifies amplification data that can be collected in a library characterization from different reaction sites.

Library 40 of FIG. 1 is depicted at the left of FIG. 3, with the variable insert indicated by "V." Portions of the library may be distributed at limiting dilution to a plurality of reaction sites, such as droplets 73. Here, only six exemplary droplets 73 are shown. However, the library may be distributed to hundreds, thousands, or more reaction sites according to the statistical accuracy desired.

Each reaction site may receive none or one or more library members. For example, four of the droplets have received either one copy of a well-formed member 48, one copy of a malformed member 50 with two A adapters, one copy of a malformed member 52 with two B adapters, or one copy of an empty member 54. Since the library has been partitioned at limiting dilution, a subset of the reaction sites, such as empty droplet 74, receive no members of the library. Another subset of the reaction sites may receive two or more library members. Here, for example, droplet 75 contains two library members, namely, library member 50 and library member 52.

The reaction sites may contain reagents for amplification of the library members. For example, each reaction site may contain a forward primer 76 and a reverse primer 77 for amplification of well-formed library members 48 (and malformed members 50-54). The reaction site also may include all of the other reagents necessary to promote amplification of the library members and amplification detection, such as dNTPs, a labeled probe for each adapter (e.g., see FIG. 7), an amplification enzyme (e.g., a polymerase, such as a heat-stable polymerase), buffer, salt, etc.

Amplification of the library members may be detected to collect amplification data from adapter-specific probes at the reaction sites. The data may be processed to identify each reaction site as double negative, A-only positive, B-only positive, or AB double positive. The different types of double positives show in FIG. 3 may or may not be distinguishable from each other according to signal strength. Further aspects of collecting and processing amplification data are described below in Example 2.

Further aspects of libraries and further aspects of digital assays, such as generating emulsions and droplets, performing nucleic acid amplification at reaction sites, and collecting and processing amplification data, are described in the materials listed above under Cross-References, which are incorporated herein by reference, particularly U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; U.S. patent application Ser. No. 13/251,016, filed Sep. 30, 2011; and U.S. patent application Ser. No. 13/548,062, filed Jul. 12, 2012.

III. Library Construction

Figure 4:
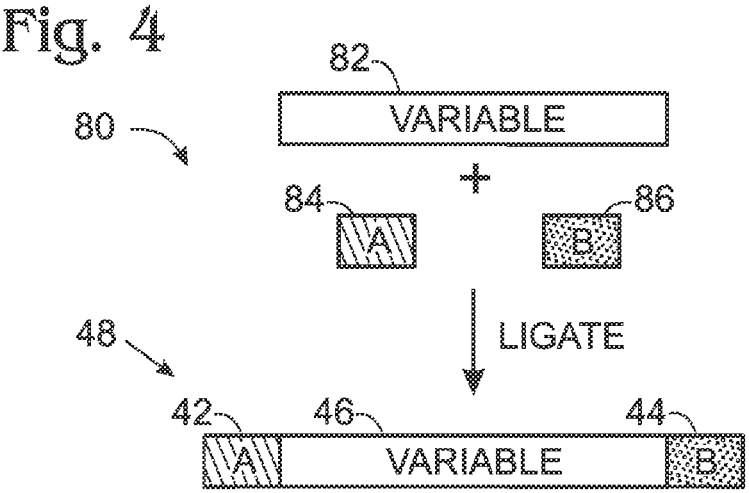
FIG. 4 is an exemplary reaction diagram illustrating an exemplary approach for constructing members of the library of FIG. 1, in accordance with aspects of the present disclosure.
Figure 5:
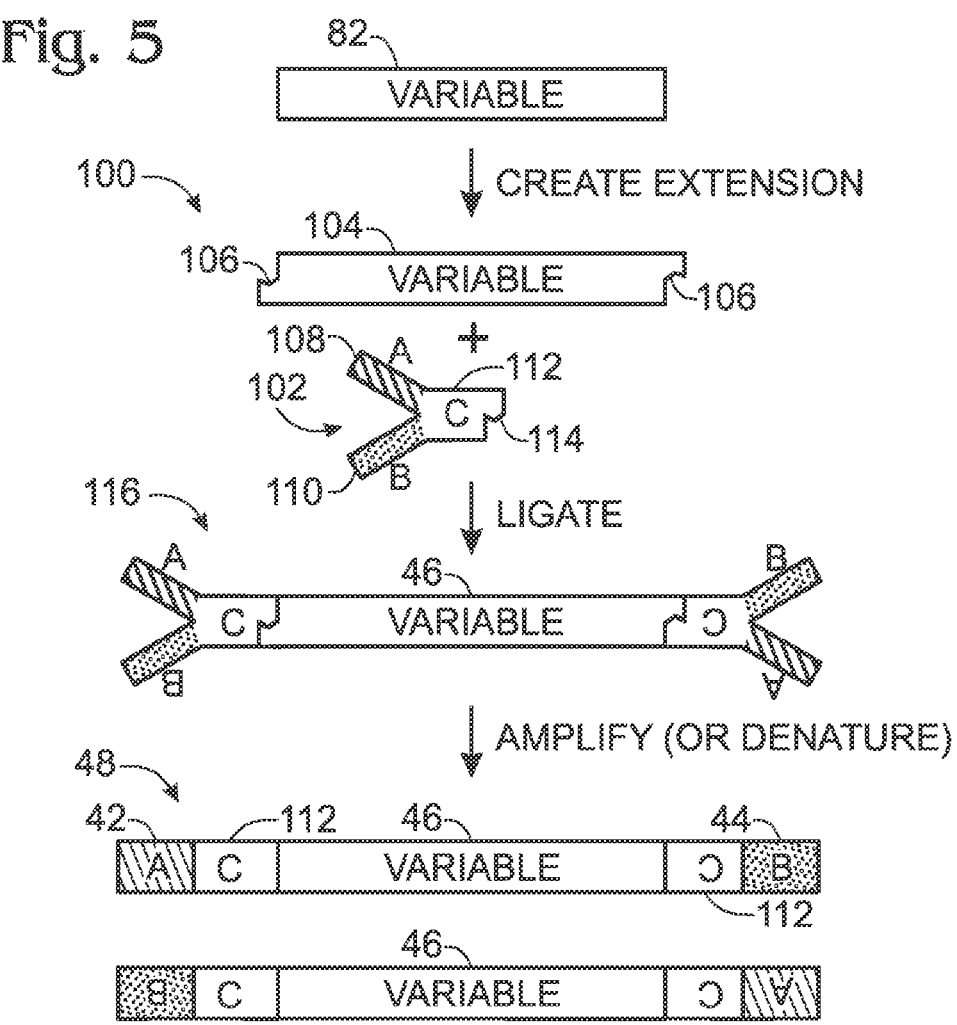
FIG. 5 is another exemplary reaction diagram illustrating another exemplary approach for constructing members of the library of FIG. 1, in accordance with aspects of the present disclosure.

This section describes selected, exemplary aspects of library construction; see FIGS. 4-6.

FIG. 4 shows an exemplary reaction strategy 80 for constructing members of the library of FIG. 1. A collection of adapter-less fragments 82 may be contacted with unlinked adapters 84, 86 and a ligase enzyme. The unlinked adapters become attached adapters that provide adapter regions 42, 44 that flank inserts 46 formed from fragments 82, to create well-formed library members 48, among others.

FIG. 5 shows another exemplary reaction strategy 100 for constructing members of the library of FIG. 1. Here, rather than using different unlinked adapters 84, 86 (see FIG. 4), the same compound adapter 102 is attached to both ends of modified fragments 104 having an extension 106. The extension may, for example, be a single nucleotide (e.g., an "A") added to both ends of fragments 82 by an adenylation reaction.

Compound adapter 102 has a general Y shape formed by a pair of oligonucleotides 108, 110. The oligonucleotides are complementary to each other at only one end of the adapter, to create a double-stranded region 112 ("C") and a pair of single-stranded regions corresponding to adapters A and B (84, 86 of FIG. 4). Double-stranded region 112 may end with an overhang 114 of one or more nucleotides, such as a single nucleotide (e.g., a "T") complementary to extension 106. With this structure, the compound adapter can ligate efficiently to modified fragments 104 but not to one another.

Ligation may produce library member precursors 116 having forked ends. The precursors may be resolved into well-formed library members 48 by amplification with adapter-specific primers (or by denaturation alone). Double-stranded region 112 may be present in the library members as an inverted repeat, as shown, forming a common sequence of each adapter and optionally providing one or more binding sites for one or more sequencing primers (and/or one or more probes).

FIG. 6 shows yet another exemplary approach for constructing members of the library of FIG. 1. A polynucleotide 120 carrying a target region 122 may serve as a template for target-specific amplification with a pair of primers 124, 126 that function as a forward primer and a reverse primer, respectively. Each primer may be described as a tailed primer or fusion primer capable of binding at a border of target 122. The primer also may provide an adapter region 128 or 130 that is linked to target region 122 by extension of each primer during target amplification to produce well-formed library members 48. A library generated via tailed primers may have a substantially constant insert sequence and may be sequenced to identify variants in the target sequence, such as rare mutations.

IV. Primers and Probes

This section describes exemplary primer and probe configurations for library characterization according to FIGS. 2 and 3; see FIG. 7.

FIG. 7 shows a schematic representation of exemplary amplification primers and probes for use in a digital amplification assay to quantify library members containing both of the different adapter regions of FIG. 1. The basic idea is to bind the adapter regions of the library members with two probes, with amplification spanning each insert. By using probes for both adapters A and B (see FIG. 1), one can measure the concentrations of well-formed library members and malformed library members, like those of FIG. 1 or other combinations. This design ensures that the presence of different adapters in the same fluid volume can be tested directly for linkage. (Co-occupancy may also occur by chance without adapter linkage; see FIG. 3 and Example 2.) With probes to each different adapter region, one can ensure identification of well-formed library members (and ill-formed libraries).

Each adapter region 42, 44 and inserts 46 may be amplified from well-formed library members 48 with one or more adapter region primers that provide a forward primer ("FP") and a reverse primer ("RP") each extendable toward insert 46 and the other adapter region. In particular, the primers may be positioned such that amplification products span the entire insert 46 and at least a flanking section of each adapter. The primers shown here also may be capable of amplifying each of the malformed library members of FIG. 1. For example, primer "FP" can bind in an amplification-competent arrangement to both ends of malformed product 50, and primer "RP" can bind similarly to both ends of malformed product 52.

Amplification products generated with the primers may be detected and distinguished with adapter-specific probes 140, 142 containing oligonucleotides 144, 146 that recognize adapter regions 42, 44, respectively. Each adapter probe may bind to the same strand of the products (e.g., both binding to the sense strand or both binding to the antisense strand) or may bind to different strands (e.g., probe 140 binding to the sense strand and probe 142 to the antisense strand, or vice versa). Each adapter region probe may (or may not) bind closer to an adjacent insert/adapter junction than the corresponding adapter region primer.

Probes 140, 142 each may include a distinct luminophore (e.g., a fluorophore), labeled here as "$L_1$" and "$L_2$." The probe also may include a quencher, labeled here as "Q." The quencher may reduce detectable light emission from the luminophore in a proximity-dependent manner. Degradation of the probe, which may occur as a result of amplification, unlinks the luminophore from the quencher, providing an increase in the signal detected. $L_1$ and $L_2$ may emit light of different wavelengths relative to each other, to provide optically distinguishable emission from the respective luminophores. Alternatively, light emission may be detected in the same channel if the luminophores produce signals of distinguishable strength, as described in U.S. patent application Ser. No. 13/548,062, filed Jul. 12, 2012, which is incorporated herein by reference. In any event, detection of a probe may include detecting light emitted by the intact probe and/or a degraded form thereof (e.g., the released luminophore).

V. EXAMPLES

The following examples describe selected aspects and embodiments of library characterization by digital assay.

These examples are intended for illustration only and should not limit the entire scope of the present disclosure.

Example 1

Exemplary Reporter Configurations for Detecting Empty Members

This example describes exemplary reporter configurations for detecting empty (and/or empty and filled) members of a library; see FIGS. 8 and 9.

FIG. 8 shows a schematic representation of exemplary amplification primers (FP, RP) and probes 140, 160 bound to empty library member 54 and well-formed library member 48. Probe 140 binds to both types of library members and thus allows determination of the collective level of both types. In contrast, probe 160 includes an oligonucleotide 162 that binds selectively to empty members of the library having a junction sequence produced by direct attachment of adapter region 42 to adapter region 44. Accordingly, data collected from probe 160 can be used to determine a level of empty library members. In some cases, the level of empty library members may be compared to a level of amplified library members detected with probe 140.

FIG. 9 shows a schematic representation similar to that of FIG. 8, except that probe 140 is replaced by an intercalating reporter 180 that binds double-stranded nucleic acid. The reporter includes a luminophore ("$L_3$") that has altered luminescence (e.g., stronger light emission) when the reporter is bound to double-stranded nucleic acid. The reporter may, for example, be ethidium bromide, SYBR Green dye, SYBR Gold dye, Oxazole Yellow (YO) dye, Thiazole Orange (TO) dye, PicoGreen (PG) dye, or the like. An intercalating reporter may be useful to characterize insert sizes of the library, since, in some configurations, the signal intensity produced by the intercalating reporter may be proportional to the size of amplicon produced at a reaction site. In some cases, the level of empty library members determined with data from probe 160 may be compared to the total level of amplifiable library members determined with data from reporter 180. In some cases, the level of amplifiable library members containing first and second adapter regions, as determined with probes that bind to each of these regions, may be compared to the total level determined with reporter 180.

Example 2

Exemplary Amplification Data and Calculations

Figure 10:
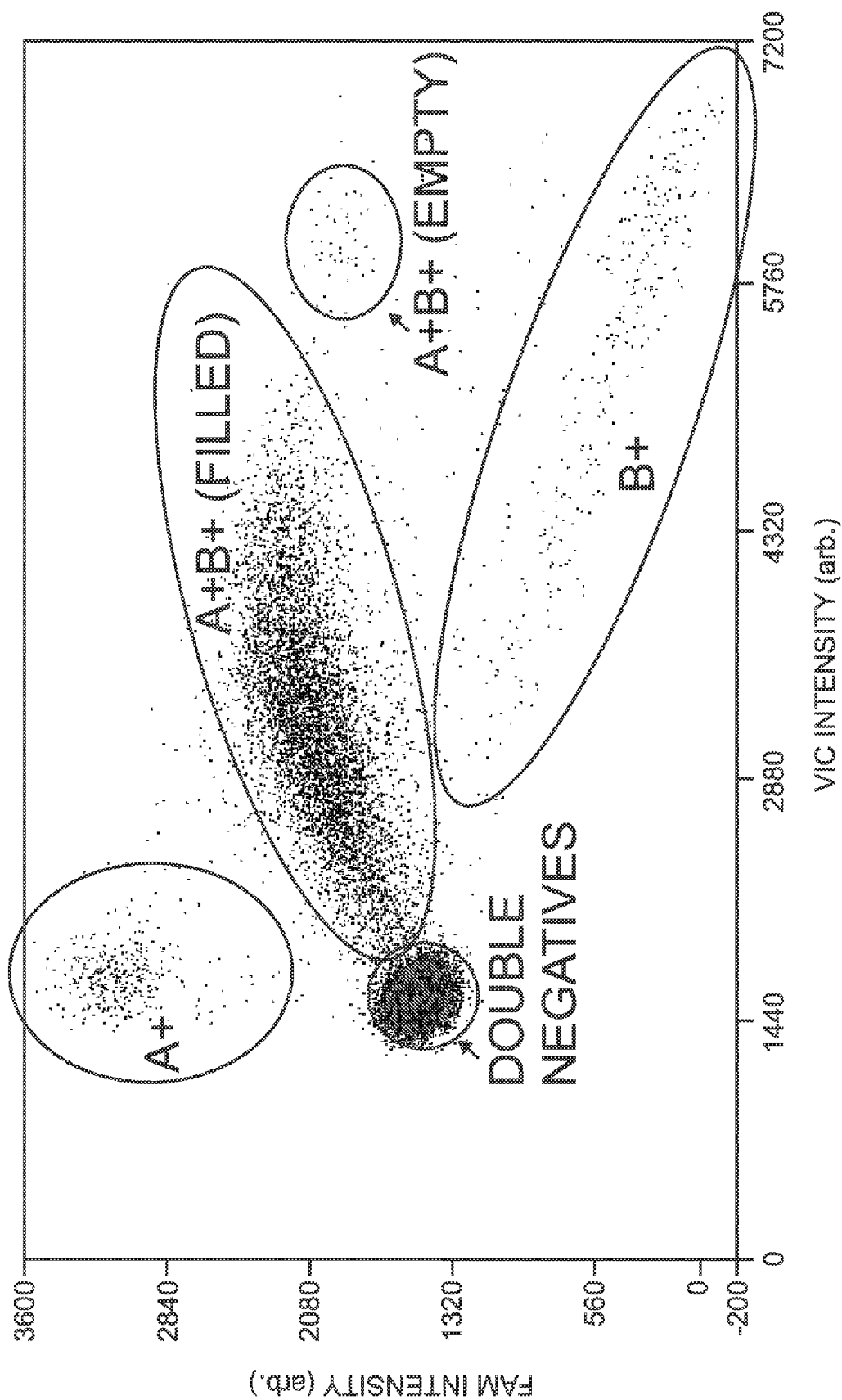
FIG. 10 is a plot of exemplary amplification data obtained with the methods of FIGS. 2 and 3 using a library constructed according to FIG. 5 and tested with the primers and probes of FIG. 7, in accordance with aspects of the present disclosure.
Figure 11:
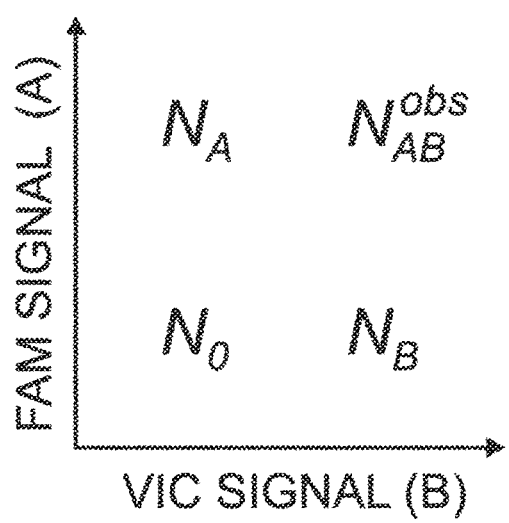
FIG. 11 is a schematic representation of the plot of FIG. 10, in accordance with aspects of the present disclosure.
Figure 12:
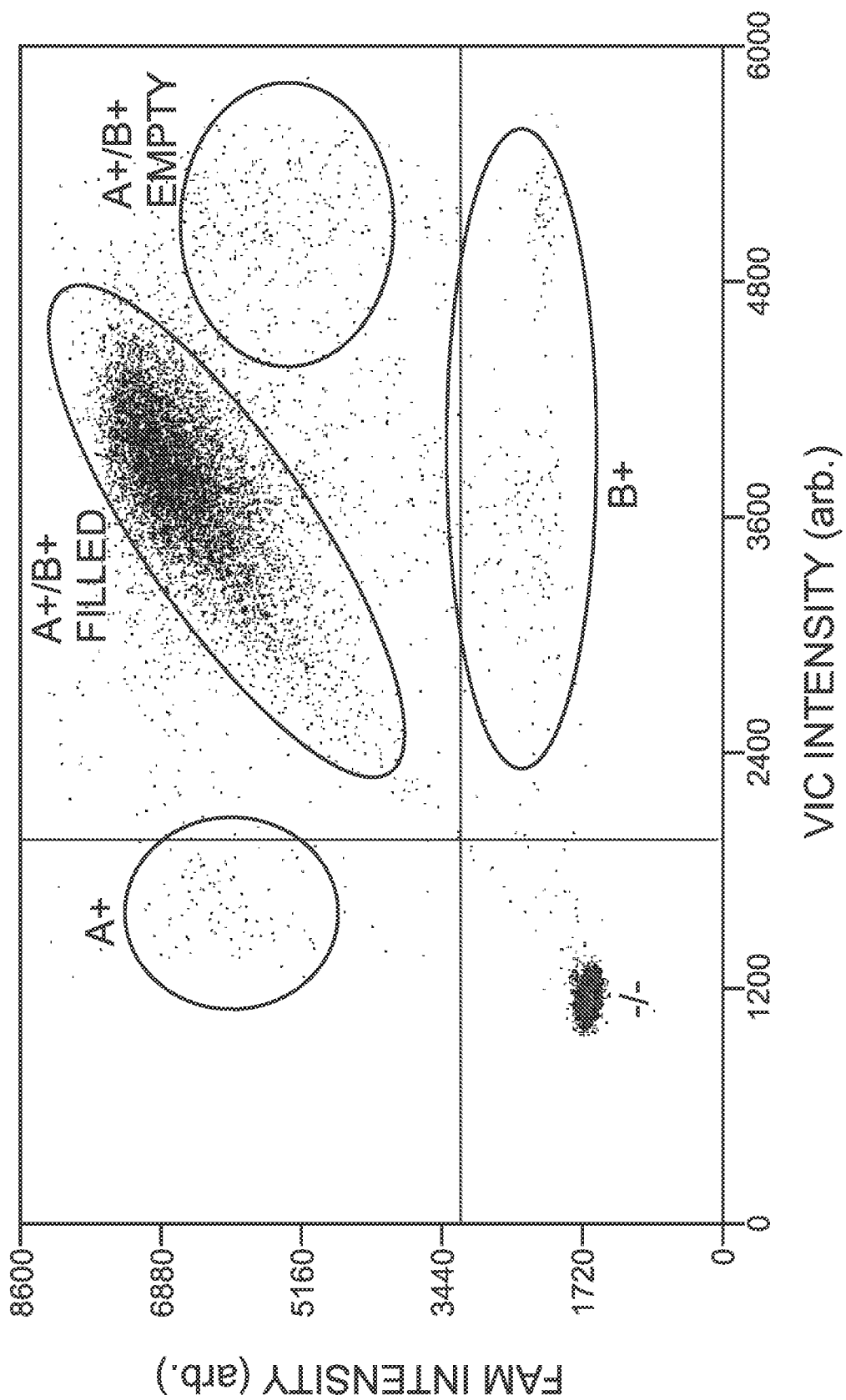
FIG. 12 is another plot of exemplary amplification data obtained with the methods of FIGS. 2 and 3 using a library constructed according to FIG. 5 and tested with the primers and probes of FIG. 7, in accordance with aspects of the present disclosure.

This example describes exemplary amplification data and calculations for a library characterization; see FIGS. 10-12.

FIG. 10 shows a two-dimensional plot of exemplary amplification data, in arbitrary intensity units, obtained from droplets with the method of FIGS. 2 and 3, using a library constructed according to FIG. 5, and tested generally according to the primers and probes of FIG. 7. Amplification of adapter sequences in the droplets was detected with the dye FAM as $L_1$ and the dye VIC as $L_2$ (see FIG. 7). Accordingly, the presence of an amplified adapter A sequence in a droplet generated a stronger FAM signal, the presence of an amplified adapter B sequence generated a stronger VIC signal, and the presence of both A and B sequences generated stronger FAM and VIC signals detected for the same droplet.

In the plot, data detected for each droplet is represented by a data point. Five clusters or populations of data points are circled and labeled for the plot according to the type(s) of adapter amplified in the corresponding droplet and/or, if both A and B are amplified, whether or not they flank an insert. The five types are as follows: (1) double-negatives ($A^-B^-$); (2) A-only positives ($A^+B^-$); (3) B-only positives ($A^-B^+$); (4) filled double-positives ($A^+B^+$, with insert); and (5) empty double-positives ($A^+B^+$, no insert) (see FIG. 3). In some cases, the double-positives may not be resolvable into a "filled" cluster and an "empty" cluster of data points.

The size and/or shape of the cluster formed by the double-positives, and particularly the filled double-positives, may be used as a quality metric for the library. Here, the cluster extends with a positive slope along a diagonal on the plot. The cluster is spread out over a wide range of signal strength, suggesting substantial variability in the amplification efficiency of library members in the droplets. Amplification efficiency will vary among library members having a variable insert depending on length, GC content, etc. of the insert. Accordingly, the "effective" distribution of inserts can be detected qualitatively by the signal level of the double positives. In other words, in the present example, the heterogeneity of inserts in the library members translates into different signal strengths for double-positives on the plot, indicating that the complexity of the library is high. In contrast, positives generally form a tight cluster, if the same sequence is being amplified in each droplet. Accordingly, the range of signal strengths of the double-positives, the tightness with which they cluster, the shape of the cluster, or the like, may provide a quality metric indicating whether library construction was sufficiently successful. Library quality thus can be assessed in the digital assay disclosed herein without additional testing. Assay optimization may be based on the separability of different insert populations.

FIG. 11 is a schematic representation of the data of FIG. 10, with the filled and empty double-positives not resolved from each other. "N" is the number of fluid volumes (droplets) observed in each cluster that are double-negative ($N_O$), positive for A only ($N_A$), positive for B only ($N_B$), or positive for both A and B ($N_{AB}^{obs}$).

Even when there is no linkage between the A and B adapters, the number of fluid volumes expected to be positive for both A and B by chance ($N_{AB}^{ch}$) is given by the following equation:

$$N_{AB}^{ch} = \frac{N_A N_B}{N_0}$$

The number of volumes due to linkage of A and B ($N_{AB}^{link}$) can be calculated as the difference between the total observed number of counts for double positives and the number of double-positives expected by chance, as follows:

$$N_{AB}^{obs} - N_{AB}^{ch} = N_{AB}^{link}$$

The concentration of linked A and B adapters (i.e., the concentration of library members containing both adapters, ($\lambda_{AB}$)) then can be calculated using the total number of volumes ($N_{tot}$) as follows:

$$\lambda_{AB} = \ln(N_{tot}) - \ln\left(N_0 + N_A + N_B + \frac{N_A N_B}{N_0}\right)$$

FIG. 12 shows another plot of exemplary amplification data obtained with the methods of FIGS. 2 and 3 using a library constructed according to FIG. 5 and tested with the primers and probes of FIG. 7. Droplet clusters are labeled generally as in FIG. 10.

Example 3

Selected Embodiments I

This example describes selected embodiments related to library analysis to quantify empty library members resulting from fusion of adapter sequences to each other in the absence of an intervening insert sequence during library construction, presented without limitation as a series of numbered paragraphs.

1. A method of quantifying empty members of a library, comprising: (A) selecting a library of members formed by ligation of at least one type of adapter with a collection of fragments, each library member having either (a) an insert from the collection flanked at each end by an adapter sequence or (b) a pair of adapter sequences ligated to each other without an intervening insert from the collection, to generate an empty member of the library; (B) determining a total level of the library members in a library sample based on amplification; (C) determining a level of the empty members in a library sample based on amplification; and (D) comparing the level of the empty members to the total level of the library members.

2. The method of paragraph 1, further comprising a step of amplifying at least a region of the library members having an insert and at least a region of the library members lacking an insert using the same pair of primers.

3. The method of paragraph 2, wherein the at least one type of adapter includes a pair of adapter types, namely, a first adapter and a second adapter.

4. The method of paragraph 3, wherein each empty member includes a sequence from the first adapter and a different sequence from the second adapter.

5. The method of paragraph 3, wherein each library member having an insert includes a sequence from the first adapter and a different sequence from the second adapter.

6. The method of paragraph 3, wherein one of the primers of the pair corresponds to the first adapter and the other primer of the pair corresponds to the second adapter.

7. The method of paragraph 1, wherein the step of determining a total level of the library members includes a step of detecting light from a first reporter, and wherein the step of determining a level of the empty members includes a step of detecting light from a second reporter that is different from the first reporter.

8. The method of paragraph 7, wherein the first reporter includes an intercalating dye.

9. The method of paragraph 7, wherein the first reporter includes a fluorophore attached to an oligonucleotide, and wherein the oligonucleotide corresponds to an adapter sequence.

10. The method of paragraph 7, wherein the second reporter includes a fluorophore attached to an oligonucleotide, and wherein the oligonucleotide binds selectively to a junction sequence formed by ligation of a pair of adapter sequences to one another.

11. The method of paragraph 1, further comprising a step of amplifying at least a region of empty members using a primer that binds selectively to a junction sequence formed by ligation of a pair of adapter sequences to one another.

12. The method of paragraph 1, wherein the steps of determining a total level of library members and a level of empty members are performed by kinetic analysis of amplification.

13. The method of paragraph 12, wherein the kinetic analysis includes real-time PCR.

14. The method of paragraph 1, wherein the steps of determining a total level of the library members and a level of the empty library members are performed by endpoint analysis of amplification in a digital amplification assay.

15. The method of paragraph 1, wherein the amplification is performed in droplets of at least one emulsion.

16. The method of paragraph 15, wherein at least one of the droplets contains no library members and at least one of the droplets contains only one library member.

17. The method of paragraph 16, wherein the droplets contain an average of less than about two library members per droplet.

18. The method of paragraph 16, wherein the droplets contain an average of less than about one library member per droplet.

19. The method of paragraph 15, wherein each step of determining includes a step of detecting light from individual droplets.

20. The method of paragraph 1, wherein each step of determining includes a step of detecting light emitted from a fluorophore, and wherein the fluorophore used in determining the total level is different than the fluorophore used in determining the level of empty members.

21. The method of paragraph 1, wherein the steps of determining both include a step of collecting amplification data from the same continuous aqueous phase or from the same droplets.

22. The method of paragraph 1, wherein the total level and the level of empty members are concentrations.

23. The method of paragraph 1, wherein the step of comparing the level of empty members to the total level includes a step of determining a ratio of levels.

24. A method of quantifying empty ligation products in a library, comprising: (A) selecting a library of ligation products formed by (a) ligation of at least one type of adapter to a collection of fragments, to generate ligation products having inserts from the collection flanked at each end by an adapter, and (b) ligation to each other without an intervening insert, to generate empty ligation products; (B) determining a total concentration of the ligation products in a library sample based on amplification of the ligation products; (C) determining a concentration of the empty ligation products in a library sample based on amplification of the empty ligation products; and (D) comparing the concentration of the empty ligation products to the total concentration of ligation products.

25. The method of paragraph 24, wherein the step of comparing includes a step of determining a ratio of the concentrations.

Example 4

Selected Embodiments II

This example describes selected embodiments related to library characterization by digital assay, presented without limitation as a series of numbered paragraphs.

1. A method of library analysis, comprising: (A) obtaining a library including inserts attached at each end to a first adapter or a second adapter; (B) distributing portions of the library at limiting dilution to a plurality of reaction sites; and (C) performing a digital amplification assay at individual reaction sites to determine a level of library members that contain both the first adapter and the second adapter.

2. A method of library analysis, comprising: (A) obtaining a library including inserts attached at each end to a first adapter or a second adapter; (B) distributing portions of the library at limiting dilution to a plurality of reaction sites; (C) amplifying inserts at the reaction sites with one or more primers that bind to the first adapter and the second adapter; (D) collecting amplification data indicating a presence or absence of an amplified first adapter sequence and a presence or absence of an amplified second adapter sequence at individual reaction sites; and (E) determining from the amplification data a level of library members that contain both the first adapter and the second adapter in a defined relative orientation.

3. A method of library analysis, comprising: (A) obtaining a library including fragments flanked at each end by a first adapter or a second adapter; (B) partitioning the library at limiting dilution into fluid volumes; (C) amplifying fragments and at least part of each adapter in the fluid volumes with one or more primers that bind to the first adapter and the second adapter; (D) collecting amplification data indicating a presence or absence of an amplified first adapter sequence and a presence or absence of an amplified second adapter sequence in the same individual fluid volumes; and (E) determining from the amplification data a level of library members that contain both the first adapter and the second adapter.

4. The method of any of paragraphs 1 to 3, wherein the library is obtained by constructing a library.

5. The method of paragraph 4, wherein the step of constructing a library includes a step of attaching one or more adapter sequences to fragments in the presence of a ligase enzyme.

6. The method of paragraph 5, wherein the step of attaching one or more adapter sequences includes a step of contacting the fragments with a compound adapter that provides both the first adapter and the second adapter.

7. The method of paragraph 6, wherein the compound adapter has a double-stranded region and a pair of single-stranded regions, and wherein the single-stranded regions are each provided by a different strand and extend from the same end of the double-stranded region.

8. The method of paragraph 6 or 7, wherein a first strand of the compound adapter provides the first adapter and a second strand of the compound adapter provides the second adapter.

9. The method of paragraph 5, wherein the step of attaching one or more adapter sequences includes a step of contacting fragments/inserts with a first adapter and a second adapter that are discrete from each other and not substantially base-paired to each other.

10. The method of paragraph 4, wherein the step of constructing a library includes a step of linking an adapter-specific sequence to fragments/inserts by DNA synthesis.

11. The method of paragraph 10, wherein the step of constructing a library includes (a) a step of contacting fragments/inserts with a pair of tailed primers that bind to the fragments/inserts and provide the first and second adapters, and (b) a step of copying the fragments/inserts by extending the tailed primers.

12. The method of any of paragraphs 1 to 3, wherein the library is received from a third party.

13. The method of any of paragraphs 1 to 12, further comprising a step of amplifying the library after the step of obtaining and before the step of distributing/partitioning.

14. The method of any of paragraphs 1 to 13, wherein the step of distributing/partitioning includes a step of generating droplets from a bulk volume containing at least a portion of the library.

15. The method of paragraph 14, wherein the step of generating droplets includes a step of forming an emulsion including the droplets disposed in a continuous phase.

16. The method of any of paragraphs 1 to 13, wherein the step of distributing/partitioning includes a step of disposing fluid volumes in a holder having an array of predefined sites each configured to receive a single fluid volume.

17. The method of paragraph 16, wherein each site is a well of the holder.

18. The method of paragraph 16 or 17, further comprising a step of contacting the fluid volumes with a same continuous liquid phase after the step of disposing the fluid volumes in the holder, wherein the fluid volumes are optionally immiscible with the liquid phase.

19. The method of any of paragraphs 1 to 18, wherein the step of distributing/partitioning the library is performed at a limiting dilution such that a plurality of the reaction sites/fluid volumes do not contain a member of the library.

20. The method of any of paragraphs 1 to 19, wherein the step of amplifying includes a step of performing a polymerase chain reaction.

21. The method of any of paragraphs 1 to 20, wherein the step of amplifying includes a step of thermally cycling the reaction sites/fluid volumes.

22. The method of any of paragraphs 1 to 21, wherein the step of amplifying includes a step of performing a ligase chain reaction.

23. The method of any of paragraphs 1 to 22, wherein the step of amplifying is performed with a first primer that binds to the first adapter and a second primer that binds to the second adapter.

24. The method of any of paragraphs 1 to 22, wherein the step of amplifying is performed with a primer that binds to the first adapter and also binds to the second adapter.

25. The method of any of paragraphs 21 to 24, wherein the step of amplifying is performed in the presence of a first labeled probe corresponding to the first adapter and a second labeled probe corresponding to the second adapter.

26. The method of paragraph 25, wherein each of the first labeled probe and the second labeled probe includes a fluorophore.

27. The method of paragraph 26, wherein each of the first labeled probe and the second labeled probe is a FRET probe.

28. The method of any of paragraphs 1 to 27, wherein the step of collecting amplification data includes a step of detecting fluorescence from reaction sites/fluid volumes.

29. The method of any of paragraphs 1 to 28, wherein the step of determining includes a step of designating each of a plurality of reaction sites/fluid volumes as positive or negative for the first adapter and as positive or negative for the second adapter.

30. The method of paragraph 29, wherein the step of designating includes a step of comparing signal strengths for the first adapter and the second adapter from individual reaction sites/fluid volumes to one or more thresholds.

31. The method of any of paragraphs 1 to 30, wherein the level determined includes a correction for occurrence of the first adapter and the second adapter in the same reaction site/fluid volume without being linked to one another.

32. The method of any of paragraphs 1 to 31, wherein the level determined is a concentration of the library members.

33. The method of any of paragraphs 1 to 32, wherein the library also includes empty members having the first adapter attached to the second adapter without an intervening insert/fragment.

34. The method of paragraph 33, wherein the level includes empty members.

35. The method of paragraph 33, wherein the level substantially excludes empty members, further comprising an optional step of determining a level of empty members in the library from the amplification data.

36. The method of any of paragraphs 1 to 35, wherein the step of determining is based on a Poisson distribution for members of the library among the reaction sites/fluid volumes.

37. The method of any of paragraphs 1 to 36, wherein the amplification data includes first signal data detected from a first fluorophore corresponding to the first adapter and second signal data detected from a second fluorophore corresponding to the second adapter, further comprising a step of plotting the first signal data against the second signal data to generate a plot.

38. The method of paragraph 36, further comprising a step of analyzing a distribution of points representing the library members in the plot.

39. The method of paragraph 38, wherein the step of analyzing a distribution of points includes a step of determining a range of the points, a linear correlation of the points, clustering of the points into one or more groups, or a combination thereof.

40. The method of paragraph 38, further comprising a step of assigning a quality metric to the library based at least in part on one or more results from the step of analyzing a distribution of points.

41. The method of any of paragraphs 1 to 40, further comprising a step of assigning a quality metric to the library based on the level of library members that contain both adapters relative to a level of library members that have only one of the adapters.

42. The method of any of paragraphs 1 to 41, further comprising a step of comparing the level of library members that contain both adapters to a level of library members that have only one of the adapters.

43. The method of any of paragraphs 1 to 42, further comprising a step of sequencing members of the library.

44. The method of any of paragraphs 1 to 43, further comprising a step of selecting an amount of the library for sequencing based on the level determined.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of library characterization, comprising:
obtaining a nucleic acid library including members each having a first adapter region and a second adapter region, wherein at least a subset of the members have an insert disposed between the first and second adapter regions;
forming partitions containing members of the library;
performing a digital assay on the partitions with an adapter region probe to generate data collected from a plurality of the partitions while members of the library are contained within the plurality of partitions, the data indicating whether a library member is present in each of the plurality of partitions; and
determining a characteristic of the library based on the data,
wherein the probe binds selectively to empty members of the library having no insert between the adapter regions, relative to members of the library having an insert.

2. The method of claim 1, wherein the step of forming partitions includes a step of forming droplets containing members of the library.

3. The method of claim 1, wherein the step of performing a digital assay includes a step of amplifying members of the library in the partitions with one or more primers that bind to the first adapter region and the second adapter region.

4. The method of claim 1, wherein the step of determining a characteristic includes a step of determining a level of empty members of the library having no insert between the adapter regions.

5. The method of claim 4, wherein the step of determining a characteristic includes a step of determining a level of members of the library that include an insert between the adapter regions.

6. The method of claim 4, wherein the probe binds selectively to a junction sequence produced by direct attachment of the first and second adapter regions to one another without an insert.

7. A method of library characterization, comprising:
obtaining a nucleic acid library including members each having a first adapter region and a second adapter region, wherein at least a subset of the members have an insert disposed between the first and second adapter regions;
forming partitions containing members of the library;
performing a digital assay on the partitions with an adapter region probe to generate data collected from a plurality of the partitions while members of the library are contained within the plurality of partitions, the data indicating whether a library member is present in each of the plurality of partitions; and
determining a characteristic of the library based on the data,
wherein the step of determining a characteristic includes a step of determining a level of empty members of the library having no insert between the adapter regions.

8. The method of claim 7, wherein the step of obtaining a nucleic acid library includes a step of attaching at least one type of adapter to opposing ends of nucleic acid fragments corresponding to the insert.

9. The method of claim 7, wherein the partitions formed are uniform in size, and wherein some of the partitions formed contain no library members and others of the partitions contain only one library member.

10. The method of claim 7, wherein the step of forming partitions includes a step of forming droplets containing members of the library.

11. The method of claim 7, wherein the step of performing a digital assay includes a step of detecting luminescence from a luminophore of the probe while the luminophore is contained by the plurality of partitions.

12. The method of claim 7, wherein the step of determining a characteristic includes a step of determining a level of members of the library that include an insert between the adapter regions.

13. The method of claim 7, wherein the step of performing a digital assay uses a first probe that binds to the first adapter region and a distinct second probe that binds to the second adapter region.

14. The method of claim 13, wherein the step of determining a characteristic includes a step of determining a level of library members containing both the first adapter region and the second adapter region.

15. The method of claim 14, wherein the level determined accounts for a presence of the first and second adapter regions in the same partitions without being linked to one another.

16. A method of library characterization, comprising:
obtaining a nucleic acid library including members each having a first adapter region and a second adapter region, wherein at least a subset of the members have an insert disposed between the first and second adapter regions;
forming partitions containing members of the library;
performing a digital assay on the partitions to generate data collected from a plurality of the partitions while members of the library are contained within the plurality of partitions, the data indicating whether a library member is present in each of the plurality of partitions; and
determining a characteristic of the library based on the data,
wherein the step of performing a digital assay uses a first probe that binds to the first adapter region and a distinct second probe that binds to the second adapter region,
wherein the step of determining a characteristic includes a step of determining a level of library members containing both the first adapter region and the second adapter region, and
wherein the step of determining a characteristic also includes a step of determining a level of library members containing the first adapter region and not the second adapter region and a level of library members containing the second adapter region and not the first adapter region.

17. The method of claim 16, wherein the partitions formed are uniform in size, and wherein some of the partitions formed contain no library members and others of the partitions contain only one library member.

18. The method of claim 16, wherein the step of forming partitions includes a step of forming droplets containing members of the library.

19. The method of claim 16, wherein the step of performing a digital assay includes a step of amplifying members of the library in the partitions with one or more primers that bind to the first adapter region and the second adapter region.

20. The method of claim 16, wherein the step of performing a digital assay includes a step of detecting luminescence from at least one luminophore of at least one of the probes while the at least one luminophore is contained by the plurality of partitions.

21. The method of claim 16, wherein the step of determining a characteristic includes a step of determining a level of empty members of the library having no insert between the adapter regions.

22. The method of claim 21, wherein the step of determining a characteristic includes a step of determining a level of members of the library that include an insert between the adapter regions.

23. A method of library characterization, comprising:
obtaining a nucleic acid library including members each having a first adapter region and a second adapter region, wherein at least a subset of the members have an insert disposed between the first and second adapter regions;
forming partitions containing members of the library;
performing a digital assay on the partitions to generate data collected from a plurality of the partitions while members of the library are contained within the plurality of partitions, the data indicating whether a library member is present in each of the plurality of partitions; and
determining a characteristic of the library based on the data,
wherein the step of performing a digital assay uses a first probe that binds to the first adapter region and a distinct second probe that binds to the second adapter region, and
wherein the step of determining a characteristic includes a step of determining a level of library members containing both the first adapter region and the second adapter region and substantially excluding empty members, and a step of determining a level of empty members from the data.

24. The method of claim 23, wherein the step of obtaining a nucleic acid library includes a step of attaching at least one type of adapter to opposing ends of nucleic acid fragments corresponding to the insert.

25. The method of claim 23, wherein the partitions formed are uniform in size, and wherein some of the partitions formed contain no library members and others of the partitions contain only one library member.

26. The method of claim 23, wherein the step of forming partitions includes a step of forming droplets containing members of the library.

27. The method of claim 23, wherein the step of performing a digital assay includes a step of amplifying members of the library in the partitions with one or more primers that bind to the first adapter region and the second adapter region.

28. The method of claim 23, wherein the step of performing a digital assay includes a step of detecting luminescence from at least one luminophore of at least one of the probes while the at least one luminophore is contained by the plurality of partitions.

29. The method of claim 23, further comprising a step of selecting an amount of the library for use in a sequencing protocol based on the characteristic.

30. The method of claim 23, wherein at least one of the probes includes a luminophore and is present in the partitions when the partitions are formed.

31. A method of library characterization, comprising:
obtaining a nucleic acid library including members each having a first constant region and a second constant region, wherein at least a subset of the members have a variable region disposed between the first and second constant regions;
forming droplets containing members of the library at limiting dilution;
amplifying members of the library in the droplets using a primer for each constant region;
detecting light emitted from the droplets; and
determining a level of empty members of the library based on the light emitted.

32. The method of claim 31, further comprising a step of determining a level of members of the library having both constant regions based on the light emitted.

33. The method of claim 31, wherein a constant region probe includes a luminophore and is present in the droplets when the droplets are formed.

* * * * *